US007540286B2

(12) United States Patent
Cross et al.

(10) Patent No.: US 7,540,286 B2
(45) Date of Patent: Jun. 2, 2009

(54) MULTIPLE DOSE CONDENSATION AEROSOL DEVICES AND METHODS OF FORMING CONDENSATION AEROSOLS

(75) Inventors: Steven D. Cross, Alamo, CA (US); Mathieu Herbette, Sunnyvale, CA (US); Andrew J. G. Kelly, Palo Alto, CA (US); Daniel J. Myers, Mountain View, CA (US); William W. Shen, Stanford, CA (US); Ryan D. Timmons, Mountain View, CA (US); Curtis Tom, San Mateo, CA (US); Justin M. Virgili, Palo Alto, CA (US); Martin J. Wensley, San Francisco, CA (US)

(73) Assignee: Alexza Pharmaceuticals, Inc., Mountain View, CA (US)

( * ) Notice: Subject to any disclaimer, the term of this patent is extended or adjusted under 35 U.S.C. 154(b) by 776 days.

(21) Appl. No.: 10/861,554

(22) Filed: Jun. 3, 2004

(65) Prior Publication Data

US 2005/0268911 A1 Dec. 8, 2005

(51) Int. Cl.
*A61M 11/00* (2006.01)

(52) U.S. Cl. ............................ 128/204.17; 128/203.26; 128/203.27

(58) Field of Classification Search ............ 128/200.24, 128/203.15, 203.24, 204.17, 203.26, 203.27, 128/202.21, 203.12
See application file for complete search history.

(56) References Cited

U.S. PATENT DOCUMENTS

| | | | |
|---|---|---|---|
| 1,239,634 | A | 9/1917 | Stuart |
| 1,535,486 | A | 4/1925 | Lundy |
| 1,803,334 | A | 5/1931 | Lehmann |
| 1,864,980 | A | 6/1932 | Curran |
| 2,084,299 | A | 6/1937 | Borden |
| 2,086,140 | A | 7/1937 | Ernst |
| 2,230,753 | A | 2/1941 | Klavehn et al. |
| 2,230,754 | A | 2/1941 | Klavehn et al. |
| 2,243,669 | A | 5/1941 | Clyne |
| 2,309,846 | A | 2/1943 | Holm |
| 2,469,656 | A | 5/1949 | Lienert |
| 2,714,649 | A | 8/1955 | Critzer |
| 2,741,812 | A | 4/1956 | Andre |
| 2,761,055 | A | 8/1956 | Ike |

(Continued)

FOREIGN PATENT DOCUMENTS

| | | |
|---|---|---|
| CA | 2152684 | 1/1996 |

(Continued)

OTHER PUBLICATIONS

U.S. Appl. No. 11/687,466, filed Mar. 16, 2007, Zaffaroni et al.

(Continued)

*Primary Examiner*—Steven O Douglas
(74) *Attorney, Agent, or Firm*—Swanson & Bratschun, L.L.C.

(57) ABSTRACT

Devices and methods of entraining a substance within an airflow are disclosed. Condensation aerosol delivery devices and methods of consistently producing multiple doses of a substance, such as a drug, having high purity, high yield, characterized by a particle size distribution appropriate for pulmonary delivery, and which can be administered to a user in a single dose are also disclosed.

55 Claims, 21 Drawing Sheets

U.S. PATENT DOCUMENTS

| | | |
|---|---|---|
| 2,887,106 A | 5/1959 | Robinson |
| 2,898,649 A | 8/1959 | Murray |
| 2,902,484 A | 9/1959 | Horclois |
| 3,043,977 A | 7/1962 | Morowitz |
| 3,080,624 A | 3/1963 | Webber, III |
| 3,164,600 A | 1/1965 | Janssen et al. |
| 3,169,095 A | 2/1965 | Thiel et al. |
| 3,200,819 A | 8/1965 | Gilbert |
| 3,219,533 A | 11/1965 | Mullins |
| 3,282,729 A | 11/1966 | Richardson et al. |
| 3,296,249 A | 1/1967 | Bell |
| 3,299,185 A | 1/1967 | Oda et al. |
| 3,371,085 A | 2/1968 | Reeder et al. |
| 3,393,197 A | 7/1968 | Pachter |
| 3,433,791 A | 3/1969 | Bentley et al. |
| 3,560,607 A | 2/1971 | Hartley et al. |
| 3,701,782 A | 10/1972 | Hester |
| 3,749,547 A | 7/1973 | Gregory et al. |
| 3,763,347 A | 10/1973 | Whitaker et al. |
| 3,773,995 A | 11/1973 | Pachter et al. |
| 3,831,606 A | 8/1974 | Damani |
| 3,847,650 A | 11/1974 | Gregory et al. |
| 3,864,326 A | 2/1975 | Babington |
| 3,894,040 A | 7/1975 | Buzby, Jr. |
| 3,909,463 A | 9/1975 | Hartman |
| 3,930,796 A | 1/1976 | Haensel |
| 3,943,941 A | 3/1976 | Boyd et al. |
| 3,949,743 A | 4/1976 | Shanbrom |
| 3,971,377 A | 7/1976 | Damani |
| 3,982,095 A | 9/1976 | Robinson |
| 3,987,052 A | 10/1976 | Hester, Jr. |
| 4,008,723 A | 2/1977 | Borthwick et al. |
| 4,020,379 A | 4/1977 | Manning |
| 4,045,156 A | 8/1977 | Chu et al. |
| 4,079,742 A | 3/1978 | Rainer et al. |
| 4,104,210 A | 8/1978 | Coran et al. |
| 4,121,583 A | 10/1978 | Chen |
| 4,141,369 A | 2/1979 | Burruss |
| 4,160,765 A | 7/1979 | Weinstock |
| 4,166,087 A | 8/1979 | Cline et al. |
| 4,183,912 A | 1/1980 | Rosenthale |
| 4,184,099 A | 1/1980 | Lindauer et al. |
| 4,190,654 A | 2/1980 | Gherardi et al. |
| 4,198,200 A | 4/1980 | Fonda et al. |
| RE30,285 E | 5/1980 | Babington |
| 4,219,031 A | 8/1980 | Rainer et al. |
| 4,229,447 A | 10/1980 | Porter |
| 4,229,931 A | 10/1980 | Schlueter et al. |
| 4,232,002 A | 11/1980 | Nogrady |
| 4,236,544 A | 12/1980 | Osaka |
| 4,251,525 A | 2/1981 | Weinstock |
| 4,276,243 A | 6/1981 | Partus |
| 4,280,629 A | 7/1981 | Slaughter |
| 4,284,089 A | 8/1981 | Ray |
| 4,286,604 A | 9/1981 | Ehretsmann et al. |
| 4,303,083 A | 12/1981 | Burruss, Jr. |
| 4,340,072 A | 7/1982 | Bolt et al. |
| 4,346,059 A | 8/1982 | Spector |
| 4,347,855 A | 9/1982 | Lanzillotti et al. |
| 4,376,767 A | 3/1983 | Sloan |
| 4,391,285 A | 7/1983 | Burnett et al. |
| 4,423,071 A | 12/1983 | Chignac et al. |
| 4,474,191 A | 10/1984 | Steiner |
| 4,484,576 A | 11/1984 | Albarda |
| 4,508,726 A | 4/1985 | Coleman |
| 4,523,589 A | 6/1985 | Krauser |
| 4,556,539 A | 12/1985 | Spector |
| 4,566,451 A | 1/1986 | Badewien |
| 4,588,425 A | 5/1986 | Usry et al. |
| 4,588,721 A | 5/1986 | Mahan |
| 4,591,615 A | 5/1986 | Aldred et al. |
| 4,605,552 A | 8/1986 | Fritschi |
| 4,627,963 A | 12/1986 | Olson |
| 4,647,428 A | 3/1987 | Gyulay |
| 4,647,433 A | 3/1987 | Spector |
| 4,654,370 A | 3/1987 | Marriott, III et al. |
| 4,683,231 A | 7/1987 | Glassman |
| 4,693,868 A | 9/1987 | Katsuda et al. |
| 4,708,151 A | 11/1987 | Shelar |
| 4,714,082 A | 12/1987 | Banerjee et al. |
| 4,722,334 A | 2/1988 | Blackmer et al. |
| 4,734,560 A | 3/1988 | Bowen |
| 4,735,217 A | 4/1988 | Gerth et al. |
| 4,735,358 A | 4/1988 | Morita et al. |
| 4,753,758 A | 6/1988 | Miller |
| 4,755,508 A | 7/1988 | Bock et al. |
| 4,756,318 A | 7/1988 | Clearman et al. |
| 4,765,347 A | 8/1988 | Sensabaugh, Jr. et al. |
| 4,771,795 A | 9/1988 | White et al. |
| 4,774,971 A | 10/1988 | Vieten |
| 4,793,365 A | 12/1988 | Sensabaugh, Jr. et al. |
| 4,793,366 A | 12/1988 | Hill |
| 4,800,903 A | 1/1989 | Ray et al. |
| 4,801,411 A | 1/1989 | Wellinghoff et al. |
| 4,814,161 A | 3/1989 | Jinks et al. |
| 4,819,665 A | 4/1989 | Roberts et al. |
| 4,848,374 A | 7/1989 | Chard et al. |
| 4,852,561 A | 8/1989 | Sperry |
| 4,853,517 A | 8/1989 | Bowen et al. |
| 4,854,331 A | 8/1989 | Banerjee et al. |
| 4,858,630 A | 8/1989 | Banerjee et al. |
| 4,863,720 A | 9/1989 | Burghart et al. |
| 4,881,541 A | 11/1989 | Eger et al. |
| 4,881,556 A | 11/1989 | Clearman et al. |
| 4,889,850 A | 12/1989 | Thornfeldt et al. |
| 4,892,109 A | 1/1990 | Strubel |
| 4,895,719 A | 1/1990 | Radhakrishnun et al. |
| 4,906,417 A | 3/1990 | Gentry |
| 4,911,157 A | 3/1990 | Miller |
| 4,917,119 A | 4/1990 | Potter et al. |
| 4,917,120 A | 4/1990 | Hill |
| 4,917,830 A | 4/1990 | Ortiz et al. |
| 4,922,901 A * | 5/1990 | Brooks et al. .......... 128/203.26 |
| 4,924,883 A | 5/1990 | Perfetti et al. |
| 4,928,714 A | 5/1990 | Shannon |
| 4,935,624 A | 6/1990 | Henion et al. |
| 4,941,483 A | 7/1990 | Ridings et al. |
| 4,947,874 A | 8/1990 | Brooks et al. |
| 4,947,875 A | 8/1990 | Brooks et al. |
| 4,950,664 A | 8/1990 | Goldberg |
| 4,955,945 A | 9/1990 | Weick |
| 4,959,380 A | 9/1990 | Wilson |
| 4,963,289 A | 10/1990 | Ortiz et al. |
| 4,968,885 A | 11/1990 | Willoughby |
| 4,984,158 A | 1/1991 | Hillsman |
| 4,989,619 A | 2/1991 | Clearman et al. |
| 5,016,425 A | 5/1991 | Weick |
| 5,017,575 A | 5/1991 | Golwyn |
| 5,019,122 A | 5/1991 | Clearman et al. |
| 5,020,548 A | 6/1991 | Farrier et al. |
| 5,027,836 A | 7/1991 | Shannon et al. |
| 5,033,483 A | 7/1991 | Clearman et al. |
| 5,038,769 A | 8/1991 | Krauser |
| 5,042,509 A | 8/1991 | Banerjee et al. |
| 5,049,389 A | 9/1991 | Radhakrishnun |
| 5,060,666 A | 10/1991 | Clearman et al. |
| 5,060,667 A | 10/1991 | Strubel |
| 5,060,671 A * | 10/1991 | Counts et al. ................ 131/329 |
| 5,067,499 A | 11/1991 | Banerjee et al. |
| 5,072,726 A | 12/1991 | Mazloomdoost et al. |
| 5,076,292 A | 12/1991 | Sensabaugh, Jr. et al. |
| 5,093,894 A | 3/1992 | Deevi et al. |
| 5,095,921 A | 3/1992 | Losee et al. |
| 5,099,861 A | 3/1992 | Clearman et al. |

| | | | | | |
|---|---|---|---|---|---|
| 5,105,831 A | 4/1992 | Banerjee et al. | 5,564,442 A | 10/1996 | MacDonald et al. |
| 5,109,180 A | 4/1992 | Boultinghouse et al. | 5,565,148 A | 10/1996 | Pendergrass |
| 5,112,598 A | 5/1992 | Biesalski | 5,577,156 A | 11/1996 | Costello |
| 5,118,494 A | 6/1992 | Schultz et al. | 5,584,701 A | 12/1996 | Lampotang et al. |
| 5,119,834 A | 6/1992 | Shannon et al. | 5,586,550 A | 12/1996 | Ivri et al. |
| 5,126,123 A | 6/1992 | Johnson | 5,591,409 A | 1/1997 | Watkins |
| 5,133,368 A | 7/1992 | Neumann et al. | 5,592,934 A | 1/1997 | Thwaites |
| 5,135,009 A | 8/1992 | Mueller et al. | 5,593,792 A | 1/1997 | Farrier et al. |
| 5,137,034 A | 8/1992 | Perfetti et al. | 5,605,146 A | 2/1997 | Sarela |
| 5,144,962 A | 9/1992 | Counts et al. | 5,605,897 A | 2/1997 | Beasley, Jr. et al. |
| 5,146,915 A | 9/1992 | Montgomery | 5,607,691 A | 3/1997 | Hale et al. |
| 5,149,538 A | 9/1992 | Granger et al. | 5,613,504 A | 3/1997 | Collins et al. |
| 5,156,170 A | 10/1992 | Clearman et al. | 5,613,505 A | 3/1997 | Campbell et al. |
| 5,160,664 A | 11/1992 | Liu | 5,619,984 A | 4/1997 | Hodson et al. |
| 5,164,740 A | 11/1992 | Ivri | 5,622,944 A | 4/1997 | Hale et al. |
| 5,166,202 A | 11/1992 | Schweizer | 5,627,178 A | 5/1997 | Chakrabarti et al. |
| 5,167,242 A | 12/1992 | Turner et al. | 5,649,554 A | 7/1997 | Sprinkel |
| 5,177,071 A | 1/1993 | Freidinger et al. | 5,655,523 A | 8/1997 | Hodson et al. |
| 5,179,966 A | 1/1993 | Losee et al. | 5,656,255 A | 8/1997 | Jones |
| 5,186,164 A | 2/1993 | Raghuprasad | 5,660,166 A | 8/1997 | Lloyd et al. |
| 5,192,548 A | 3/1993 | Velasquez et al. | 5,666,977 A | 9/1997 | Higgins et al. |
| 5,224,498 A | 7/1993 | Deevi et al. | 5,690,809 A | 11/1997 | Subramaniam et al. |
| 5,226,411 A | 7/1993 | Levine | 5,694,919 A | 12/1997 | Rubsamen et al. |
| 5,229,120 A | 7/1993 | DeVincent | 5,718,222 A | 2/1998 | Lloyd et al. |
| 5,229,382 A | 7/1993 | Chakrabarti et al. | 5,724,957 A | 3/1998 | Rubsamen et al. |
| 5,240,922 A | 8/1993 | O'Neill | 5,725,756 A | 3/1998 | Subramaniam et al. |
| 5,249,586 A | 10/1993 | Morgan et al. | 5,733,572 A | 3/1998 | Unger et al. |
| 5,255,674 A | 10/1993 | Oftedal et al. | 5,735,263 A | 4/1998 | Rubsamen et al. |
| 5,261,424 A | 11/1993 | Sprinkel, Jr. | 5,738,865 A | 4/1998 | Baichwal et al. |
| 5,264,433 A | 11/1993 | Sato et al. | 5,743,250 A | 4/1998 | Gonda et al. |
| 5,269,327 A | 12/1993 | Counts et al. | 5,743,251 A | 4/1998 | Howell et al. |
| 5,284,133 A | 2/1994 | Burns et al. | 5,744,469 A | 4/1998 | Tran |
| 5,285,798 A | 2/1994 | Banerjee et al. | 5,747,001 A | 5/1998 | Wiedmann et al. |
| 5,292,499 A | 3/1994 | Evans et al. | 5,756,449 A | 5/1998 | Andersen et al. |
| 5,322,075 A | 6/1994 | Deevi et al. | 5,758,637 A | 6/1998 | Ivri et al. |
| 5,333,106 A | 7/1994 | Lanpher et al. | 5,767,117 A | 6/1998 | Moskowitz et al. |
| 5,345,951 A | 9/1994 | Serrano et al. | 5,769,621 A | 6/1998 | Early et al. |
| 5,357,984 A | 10/1994 | Farrier et al. | 5,770,222 A | 6/1998 | Unger et al. |
| 5,363,842 A | 11/1994 | Mishelevich et al. | 5,771,882 A | 6/1998 | Psaros et al. |
| 5,364,838 A | 11/1994 | Rubsamen | 5,776,928 A | 7/1998 | Beasley, Jr. |
| 5,366,770 A | 11/1994 | Wang | 5,804,212 A | 9/1998 | Illum |
| 5,372,148 A | 12/1994 | McCafferty et al. | 5,809,997 A | 9/1998 | Wolf |
| 5,376,386 A | 12/1994 | Ganderton et al. | 5,817,656 A | 10/1998 | Beasley, Jr. et al. |
| 5,388,574 A | 2/1995 | Ingebrethsen | 5,819,756 A | 10/1998 | Mierlordt |
| 5,391,081 A | 2/1995 | Lampotang et al. | 5,823,178 A | 10/1998 | Lloyd et al. |
| 5,399,574 A | 3/1995 | Robertson et al. | 5,829,436 A | 11/1998 | Rubsamen et al. |
| 5,400,808 A | 3/1995 | Turner et al. | 5,833,891 A | 11/1998 | Subramaniam et al. |
| 5,400,969 A | 3/1995 | Keene | 5,840,246 A | 11/1998 | Hammons et al. |
| 5,402,517 A | 3/1995 | Gillett et al. | 5,855,564 A | 1/1999 | Ruskewicz |
| 5,408,574 A | 4/1995 | Deevi et al. | 5,855,913 A | 1/1999 | Hanes et al. |
| 5,431,167 A | 7/1995 | Savord | 5,865,185 A | 2/1999 | Collins et al. |
| 5,436,230 A | 7/1995 | Soudant et al. | 5,874,064 A | 2/1999 | Edwards et al. |
| 5,451,408 A | 9/1995 | Mezei et al. | 5,874,481 A | 2/1999 | Weers et al. |
| 5,455,043 A | 10/1995 | Fischel-Ghodsian | 5,875,776 A | 3/1999 | Vaghefi |
| 5,456,247 A | 10/1995 | Shilling et al. | 5,878,752 A | 3/1999 | Adams et al. |
| 5,456,677 A | 10/1995 | Spector | 5,884,620 A | 3/1999 | Gonda et al. |
| 5,457,100 A | 10/1995 | Daniel | 5,890,908 A | 4/1999 | Lampotang et al. |
| 5,457,101 A | 10/1995 | Greenwood et al. | 5,894,841 A | 4/1999 | Voges |
| 5,459,137 A | 10/1995 | Andrasi et al. | 5,900,249 A | 5/1999 | Smith |
| 5,462,740 A | 10/1995 | Evenstad et al. | 5,904,900 A | 5/1999 | Bleuse et al. |
| 5,468,936 A | 11/1995 | Deevi et al. | 5,906,811 A | 5/1999 | Hersh |
| 5,479,948 A * | 1/1996 | Counts et al. ............... 131/194 | 5,907,075 A | 5/1999 | Subramaniam et al. |
| 5,501,236 A | 3/1996 | Hill et al. | 5,910,301 A | 6/1999 | Farr et al. |
| 5,505,214 A | 4/1996 | Collins et al. | 5,915,378 A | 6/1999 | Lloyd et al. |
| 5,507,277 A | 4/1996 | Rubsamen et al. | 5,918,595 A | 7/1999 | Olsson |
| 5,511,726 A | 4/1996 | Greenspan et al. | 5,928,520 A | 7/1999 | Haumesser |
| 5,519,019 A | 5/1996 | Andrasi et al. | 5,929,093 A | 7/1999 | Pang et al. |
| 5,522,385 A | 6/1996 | Lloyd et al. | 5,934,272 A | 8/1999 | Lloyd et al. |
| 5,525,329 A | 6/1996 | Snyder et al. | 5,934,289 A | 8/1999 | Watkins et al. |
| 5,537,507 A | 7/1996 | Mariner et al. | 5,935,604 A | 8/1999 | Illum |
| 5,538,020 A | 7/1996 | Farrier et al. | 5,938,117 A | 8/1999 | Ivri |
| 5,543,434 A | 8/1996 | Weg | 5,939,100 A | 8/1999 | Albrechtsen et al. |
| 5,544,646 A | 8/1996 | Lloyd et al. | 5,941,240 A | 8/1999 | Gonda et al. |

| | | | | | | |
|---|---|---|---|---|---|---|
| 5,944,012 | A | 8/1999 | Pera | 6,516,796 | B1 | 2/2003 | Cox et al. |
| 5,957,124 | A | 9/1999 | Lloyd et al. | 6,526,969 | B2 * | 3/2003 | Nilsson et al. ......... 128/203.15 |
| 5,960,792 | A | 10/1999 | Lloyd et al. | 6,557,552 | B1 | 5/2003 | Cox et al. |
| 5,970,973 | A | 10/1999 | Gonda et al. | 6,561,186 | B2 | 5/2003 | Casper et al. |
| 5,971,951 | A | 10/1999 | Ruskewicz | 6,568,390 | B2 | 5/2003 | Nichols et al. |
| 5,985,309 | A | 11/1999 | Edwards et al. | 6,591,839 | B2 | 7/2003 | Meyer et al. |
| 5,993,805 | A | 11/1999 | Sutton et al. | 6,632,047 | B2 | 10/2003 | Vinegar et al. |
| 6,004,516 | A | 12/1999 | Rasouli et al. | 6,638,981 | B2 | 10/2003 | Williams et al. |
| 6,004,970 | A | 12/1999 | O'Malley et al. | 6,648,950 | B2 | 11/2003 | Lee et al. |
| 6,008,214 | A | 12/1999 | Kwon et al. | 6,671,945 | B2 | 1/2004 | Gerber et al. |
| 6,008,216 | A | 12/1999 | Chakrabarti et al. | 6,680,668 | B2 | 1/2004 | Gerber et al. |
| 6,013,050 | A | 1/2000 | Bellhouse et al. | 6,681,769 | B2 | 1/2004 | Sprinkel et al. |
| 6,014,969 | A | 1/2000 | Lloyd et al. | 6,681,998 | B2 | 1/2004 | Sharpe et al. |
| 6,014,970 | A | 1/2000 | Ivri et al. | 6,682,716 | B2 | 1/2004 | Hodges et al. |
| 6,041,777 | A | 3/2000 | Faithfull et al. | 6,684,880 | B2 | 2/2004 | Trueba et al. |
| 6,044,777 | A | 4/2000 | Walsh | 6,688,313 | B2 | 2/2004 | Wrenn et al. |
| 6,048,550 | A | 4/2000 | Chan et al. | 6,694,975 | B2 | 2/2004 | Schuster et al. |
| 6,048,857 | A | 4/2000 | Ellinwood, Jr. et al. | 6,701,921 | B2 | 3/2004 | Sprinkel et al. |
| 6,050,260 | A | 4/2000 | Daniell et al. | 6,701,922 | B2 | 3/2004 | Hindle et al. |
| 6,051,257 | A | 4/2000 | Kodas et al. | 6,715,487 | B2 | 4/2004 | Nichols et al. |
| 6,051,566 | A | 4/2000 | Bianco | 6,716,415 | B2 | 4/2004 | Rabinowitz et al. |
| 6,053,176 | A | 4/2000 | Adams et al. | 6,716,416 | B2 | 4/2004 | Rabinowitz et al. |
| RE36,744 | E | 6/2000 | Goldberg | 6,716,417 | B2 | 4/2004 | Rabinowitz et al. |
| 6,085,026 | A | 7/2000 | Hammons et al. | 6,728,478 | B2 | 4/2004 | Cox et al. |
| 6,089,857 | A | 7/2000 | Matsuura et al. | 6,737,042 | B2 | 5/2004 | Rabinowitz et al. |
| 6,090,212 | A | 7/2000 | Mahawili | 6,737,043 | B2 | 5/2004 | Rabinowitz et al. |
| 6,095,134 | A | 8/2000 | Sievers et al. | 6,740,307 | B2 | 5/2004 | Rabinowitz et al. |
| 6,095,153 | A | 8/2000 | Kessler et al. | 6,740,308 | B2 | 5/2004 | Rabinowitz et al. |
| 6,098,620 | A | 8/2000 | Lloyd et al. | 6,740,309 | B2 | 5/2004 | Rabinowitz et al. |
| 6,102,036 | A * | 8/2000 | Slutsky et al. ......... 128/203.15 | 6,743,415 | B2 | 6/2004 | Rabinowitz et al. |
| 6,113,795 | A | 9/2000 | Subramaniam et al. | 6,759,029 | B2 | 7/2004 | Hale et al. |
| 6,117,866 | A | 9/2000 | Bondinell et al. | 6,772,756 | B2 | 8/2004 | Shayan |
| 6,125,853 | A | 10/2000 | Susa et al. | 6,772,757 | B2 | 8/2004 | Sprinkel, Jr. et al. |
| 6,126,919 | A | 10/2000 | Stefely et al. | 6,776,978 | B2 | 8/2004 | Rabinowitz et al. |
| 6,131,566 | A | 10/2000 | Ashurst et al. | 6,779,520 | B2 | 8/2004 | Genova et al. |
| 6,131,570 | A | 10/2000 | Schuster et al. | 6,780,399 | B2 | 8/2004 | Rabinowitz et al. |
| 6,133,327 | A | 10/2000 | Kimura et al. | 6,780,400 | B2 | 8/2004 | Rabinowitz et al. |
| 6,135,369 | A | 10/2000 | Prendergast et al. | 6,783,753 | B2 | 8/2004 | Rabinowitz et al. |
| 6,155,268 | A | 12/2000 | Takeuchi | 6,797,259 | B2 | 9/2004 | Rabinowitz et al. |
| 6,158,431 | A | 12/2000 | Poole | 6,803,031 | B2 | 10/2004 | Rabinowitz et al. |
| 6,178,969 | B1 | 1/2001 | St. Charles | 6,805,853 | B2 | 10/2004 | Rabinowitz et al. |
| 6,211,171 | B1 | 4/2001 | Sawynok et al. | 6,805,854 | B2 | 10/2004 | Hale et al. |
| 6,234,167 | B1 | 5/2001 | Cox et al. | 6,814,954 | B2 | 11/2004 | Rabinowitz et al. |
| 6,241,969 | B1 | 6/2001 | Saidi et al. | 6,814,955 | B2 | 11/2004 | Rabinowitz et al. |
| 6,250,298 | B1 | 6/2001 | Gonda et al. | 6,855,310 | B2 | 2/2005 | Rabinowitz et al. |
| 6,250,301 | B1 | 6/2001 | Pate | 6,884,408 | B2 | 4/2005 | Rabinowitz et al. |
| 6,255,334 | B1 | 7/2001 | Sands | 6,994,843 | B2 | 2/2006 | Rabinowitz et al. |
| 6,263,872 | B1 | 7/2001 | Schuster et al. | 7,005,121 | B2 | 2/2006 | Rabinowitz et al. |
| 6,264,922 | B1 | 7/2001 | Wood et al. | 7,005,122 | B2 | 2/2006 | Hale et al. |
| 6,284,287 | B1 | 9/2001 | Sarlikiotis et al. | 7,008,615 | B2 | 3/2006 | Rabinowitz et al. |
| 6,290,986 | B1 | 9/2001 | Murdock et al. | 7,008,616 | B2 | 3/2006 | Rabinowitz et al. |
| 6,299,900 | B1 | 10/2001 | Reed et al. | 7,011,819 | B2 | 3/2006 | Hale et al. |
| 6,300,710 | B1 | 10/2001 | Nakamori | 7,011,820 | B2 | 3/2006 | Rabinowitz et al. |
| 6,306,431 | B1 | 10/2001 | Zhang et al. | 7,014,840 | B2 | 3/2006 | Hale et al. |
| 6,309,668 | B1 | 10/2001 | Bastin et al. | 7,014,841 | B2 | 3/2006 | Rabinowitz et al. |
| 6,309,986 | B1 | 10/2001 | Flashinski et al. | 7,018,619 | B2 | 3/2006 | Rabinowitz et al. |
| 6,313,176 | B1 | 11/2001 | Ellinwood, Jr. et al. | 7,018,620 | B2 | 3/2006 | Rabinowitz et al. |
| 6,325,475 | B1 | 12/2001 | Hayes et al. | 7,018,621 | B2 | 3/2006 | Hale et al. |
| 6,328,033 | B1 * | 12/2001 | Avrahami ............... 128/203.15 | 7,022,312 | B2 | 4/2006 | Rabinowitz et al. |
| 6,376,550 | B1 | 4/2002 | Raber et al. | 7,029,658 | B2 | 4/2006 | Rabinowitz et al. |
| 6,390,453 | B1 | 5/2002 | Frederickson et al. | 7,033,575 | B2 | 4/2006 | Rabinowitz et al. |
| 6,408,854 | B1 | 6/2002 | Gonda et al. | 7,040,314 | B2 | 5/2006 | Nguyen et al. |
| 6,413,930 | B1 | 7/2002 | Ratti et al. | 7,045,118 | B2 | 5/2006 | Rabinowitz et al. |
| 6,420,351 | B1 | 7/2002 | Tsai et al. | 7,045,119 | B2 | 5/2006 | Rabinowitz et al. |
| 6,431,166 | B2 | 8/2002 | Gonda et al. | 7,048,909 | B2 | 5/2006 | Rabinowitz et al. |
| 6,443,152 | B1 | 9/2002 | Lockhart et al. | 7,052,679 | B2 | 5/2006 | Rabinowitz et al. |
| 6,444,665 | B1 | 9/2002 | Helton et al. | 7,052,680 | B2 | 5/2006 | Rabinowitz et al. |
| 6,461,591 | B1 | 10/2002 | Keller et al. | 7,060,254 | B2 | 6/2006 | Rabinowitz et al. |
| 6,479,074 | B2 | 11/2002 | Murdock et al. | 7,060,255 | B2 | 6/2006 | Rabinowitz et al. |
| 6,491,233 | B2 | 12/2002 | Nichols | 7,063,830 | B2 | 6/2006 | Rabinowitz et al. |
| 6,501,052 | B2 | 12/2002 | Cox et al. | 7,063,831 | B2 | 6/2006 | Rabinowitz et al. |
| 6,506,762 | B1 | 1/2003 | Horvath et al. | 7,063,832 | B2 | 6/2006 | Rabinowitz et al. |
| 6,514,482 | B1 | 2/2003 | Bartus et al. | 7,067,114 | B2 | 6/2006 | Rabinowitz et al. |

| | | | |
|---|---|---|---|
| 7,070,761 B2 | 7/2006 | Rabinowitz et al. | |
| 7,070,762 B2 | 7/2006 | Rabinowitz et al. | |
| 7,070,763 B2 | 7/2006 | Rabinowitz et al. | |
| 7,070,764 B2 | 7/2006 | Rabinowitz et al. | |
| 7,070,765 B2 | 7/2006 | Rabinowitz et al. | |
| 7,070,766 B2 | 7/2006 | Rabinowitz et al. | |
| 7,078,016 B2 | 7/2006 | Rabinowitz et al. | |
| 7,078,017 B2 | 7/2006 | Rabinowitz et al. | |
| 7,078,018 B2 | 7/2006 | Rabinowitz et al. | |
| 7,078,019 B2 | 7/2006 | Rabinowitz et al. | |
| 7,078,020 B2 | 7/2006 | Rabinowitz et al. | |
| 7,087,216 B2 | 8/2006 | Rabinowitz et al. | |
| 7,087,217 B2 | 8/2006 | Rabinowitz et al. | |
| 7,087,218 B2 | 8/2006 | Rabinowitz et al. | |
| 7,090,830 B2 | 8/2006 | Hale et al. | |
| 7,094,392 B2 | 8/2006 | Rabinowitz et al. | |
| 7,108,847 B2 | 9/2006 | Rabinowitz et al. | |
| 7,115,250 B2 | 10/2006 | Rabinowitz et al. | |
| 7,169,378 B2 | 1/2007 | Rabinowitz et al. | |
| 7,402,777 B2 | 7/2008 | Hale et al. | |
| 2001/0020147 A1 | 9/2001 | Staniforth et al. | |
| 2001/0039262 A1 | 11/2001 | Venkataraman | |
| 2001/0042546 A1 | 11/2001 | Umeda et al. | |
| 2002/0031480 A1 | 3/2002 | Peart et al. | |
| 2002/0037828 A1 | 3/2002 | Wilson et al. | |
| 2002/0058009 A1 | 5/2002 | Bartus et al. | |
| 2002/0061281 A1 | 5/2002 | Osbakken et al. | |
| 2002/0078955 A1 | 6/2002 | Nichols et al. | |
| 2002/0086852 A1 | 7/2002 | Cantor | |
| 2002/0097139 A1 | 7/2002 | Gerber et al. | |
| 2002/0112723 A1 | 8/2002 | Schuster et al. | |
| 2002/0117175 A1 | 8/2002 | Kottayil et al. | |
| 2002/0176841 A1 | 11/2002 | Barker et al. | |
| 2003/0004142 A1 | 1/2003 | Prior et al. | |
| 2003/0015196 A1 | 1/2003 | Hodges et al. | |
| 2003/0015197 A1 | 1/2003 | Hale et al. | |
| 2003/0032638 A1 | 2/2003 | Kim et al. | |
| 2003/0033055 A1 | 2/2003 | McRae et al. | |
| 2003/0049025 A1 | 3/2003 | Neumann et al. | |
| 2003/0051728 A1 | 3/2003 | Lloyd et al. | |
| 2003/0062042 A1 | 4/2003 | Wensley et al. | |
| 2003/0106551 A1 | 6/2003 | Sprinkel et al. | |
| 2003/0118512 A1 | 6/2003 | Shen | |
| 2003/0121906 A1 | 7/2003 | Abbott et al. | |
| 2003/0131843 A1 | 7/2003 | Lu | |
| 2003/0132219 A1 | 7/2003 | Cox et al. | |
| 2003/0138508 A1 | 7/2003 | Novack et al. | |
| 2003/0156829 A1 | 8/2003 | Cox et al. | |
| 2003/0209240 A1 | 11/2003 | Hale et al. | |
| 2004/0009128 A1 | 1/2004 | Rabinowitz et al. | |
| 2004/0016427 A1 | 1/2004 | Byron et al. | |
| 2004/0035409 A1 | 2/2004 | Harwig et al. | |
| 2004/0055504 A1 | 3/2004 | Lee et al. | |
| 2004/0081624 A1 | 4/2004 | Nguyen et al. | |
| 2004/0096402 A1 | 5/2004 | Hodges et al. | |
| 2004/0099266 A1 | 5/2004 | Cross et al. | |
| 2004/0101481 A1 | 5/2004 | Hale et al. | |
| 2004/0102434 A1 | 5/2004 | Hale et al. | |
| 2004/0105818 A1 | 6/2004 | Every et al. | |
| 2004/0105819 A1 | 6/2004 | Hale et al. | |
| 2004/0234699 A1 | 11/2004 | Hale et al. | |
| 2004/0234914 A1 | 11/2004 | Hale et al. | |
| 2004/0234916 A1 | 11/2004 | Hale et al. | |
| 2005/0034723 A1 | 2/2005 | Bennett et al. | |
| 2005/0037506 A1 | 2/2005 | Hale et al. | |
| 2005/0079166 A1 | 4/2005 | Damani et al. | |
| 2005/0126562 A1 | 6/2005 | Rabinowitz et al. | |
| 2005/0131739 A1 | 6/2005 | Rabinowitz et al. | |
| 2006/0032496 A1 | 2/2006 | Hale et al. | |
| 2006/0032501 A1 | 2/2006 | Hale et al. | |
| 2006/0120962 A1 | 6/2006 | Rabinowitz et al. | |
| 2006/0153779 A1 | 7/2006 | Rabinowitz et al. | |
| 2006/0177382 A1 | 8/2006 | Rabinowitz et al. | |
| 2006/0193788 A1 | 8/2006 | Hale et al. | |
| 2006/0216243 A1 | 9/2006 | Rabinowitz et al. | |
| 2006/0216244 A1 | 9/2006 | Rabinowitz et al. | |
| 2006/0233717 A1 | 10/2006 | Hale et al. | |
| 2006/0233718 A1 | 10/2006 | Rabinowitz et al. | |
| 2006/0233719 A1 | 10/2006 | Rabinowitz et al. | |
| 2006/0239936 A1 | 10/2006 | Rabinowitz et al. | |
| 2006/0246011 A1 | 11/2006 | Rabinowitz et al. | |
| 2006/0246012 A1 | 11/2006 | Rabinowitz et al. | |
| 2006/0251587 A1 | 11/2006 | Rabinowitz et al. | |
| 2006/0251588 A1 | 11/2006 | Rabinowitz et al. | |
| 2006/0257328 A1 | 11/2006 | Rabinowitz et al. | |
| 2006/0257329 A1 | 11/2006 | Rabinowitz et al. | |
| 2006/0269486 A1 | 11/2006 | Rabinowitz et al. | |
| 2006/0269487 A1 | 11/2006 | Rabinowitz et al. | |
| 2006/0280692 A1 | 12/2006 | Rabinowitz et al. | |
| 2006/0286042 A1 | 12/2006 | Rabinowitz et al. | |
| 2006/0286043 A1 | 12/2006 | Rabinowitz et al. | |
| 2007/0014737 A1 | 1/2007 | Rabinowitz et al. | |
| 2007/0028916 A1 | 2/2007 | Hale et al. | |
| 2007/0031340 A1 | 2/2007 | Hale et al. | |
| 2007/0122353 A1 | 5/2007 | Hale et al. | |
| 2007/0140982 A1 | 6/2007 | Every et al. | |
| 2007/0178052 A1 | 8/2007 | Rabinowitz et al. | |
| 2007/0286816 A1 | 12/2007 | Hale et al. | |
| 2008/0110872 A1 | 5/2008 | Hale et al. | |
| 2008/0175796 A1 | 7/2008 | Rabinowitz et al. | |
| 2008/0216828 A1 | 9/2008 | Wensley | |

FOREIGN PATENT DOCUMENTS

| | | | |
|---|---|---|---|
| CN | 1082365 | 2/1994 | |
| CN | 1176075 | 3/1998 | |
| DE | 198 54 007 | 5/2000 | |
| EP | 0 039 369 | 11/1981 | |
| EP | 0 274 431 | 7/1988 | |
| EP | 0 277 519 | 8/1988 | |
| EP | 0 358 114 | 3/1990 | |
| EP | 0 430 559 | 6/1991 | |
| EP | 0 492 485 | 7/1992 | |
| EP | 0 606 486 | 7/1994 | |
| EP | 0 734 719 | 2/1996 | |
| EP | 0 967 214 | 12/1999 | |
| EP | 1 080 720 | 3/2001 | |
| EP | 1 177 973 | 2/2002 | |
| EP | 0 808 635 B1 | 7/2003 | |
| FR | 921 852 A | 5/1947 | |
| FR | 2 428 068 A | 1/1980 | |
| GB | 502 761 | 1/1938 | |
| GB | 903 866 | 8/1962 | |
| GB | 1 366 041 | 9/1974 | |
| GB | 2 108 390 | 5/1983 | |
| GB | 2 122 903 | 1/1984 | |
| HU | 200105 B | 10/1988 | |
| HU | 219392 B | 6/1993 | |
| WO | WO 85/00520 | 2/1985 | |
| WO | WO 88/08304 | 11/1988 | |
| WO | WO 90/02737 | 3/1990 | |
| WO | WO 90/07333 | 7/1990 | |
| WO | WO 91/07947 | 6/1991 | |
| WO | WO 91/18525 | 12/1991 | |
| WO | WO 92/05781 | 4/1992 | |
| WO | WO 92/15353 | 9/1992 | |
| WO | WO 92/19303 | 11/1992 | |
| WO | WO 93/12823 | 7/1993 | |
| WO | WO 94/09842 | 4/1994 | |
| WO | WO 94/16717 | 8/1994 | |
| WO | WO 94/16757 | 8/1994 | |
| WO | WO 94/16759 | 8/1994 | |
| WO | WO 94/17369 | 8/1994 | |
| WO | WO 94/17370 | 8/1994 | |
| WO | WO 94/27576 | 12/1994 | |
| WO | WO 94/27653 | 12/1994 | |

| | | |
|---|---|---|
| WO | WO 95/31182 | 11/1995 |
| WO | WO 96/00069 | 1/1996 |
| WO | WO 96/00070 | 1/1996 |
| WO | WO 96/00071 | 1/1996 |
| WO | WO 96/09846 | 4/1996 |
| WO | WO 96/10663 | 4/1996 |
| WO | WO 96/13161 | 5/1996 |
| WO | WO 96/13290 | 5/1996 |
| WO | WO 96/13291 | 5/1996 |
| WO | WO 96/13292 | 5/1996 |
| WO | WO 96/30068 | 10/1996 |
| WO | WO 96/31198 | 10/1996 |
| WO | WO 96/37198 | 11/1996 |
| WO | WO 97/16181 | 5/1997 |
| WO | WO 97/17948 | 5/1997 |
| WO | WO 97/23221 | 7/1997 |
| WO | WO 97/27804 | 8/1997 |
| WO | WO 97/31691 | 9/1997 |
| WO | WO 97/35562 | 10/1997 |
| WO | WO 97/35582 | 10/1997 |
| WO | WO 97/36574 | 10/1997 |
| WO | WO 97/40819 | 11/1997 |
| WO | WO 97/49690 | 12/1997 |
| WO | WO 98/02186 | 1/1998 |
| WO | WO 98/16205 | 4/1998 |
| WO | WO 98/22170 | 5/1998 |
| WO | WO 98/29110 | 7/1998 |
| WO | WO 98/31346 | 7/1998 |
| WO | WO 98/34595 | 8/1998 |
| WO | WO 98/36651 | 8/1998 |
| WO | WO 98/37896 | 9/1998 |
| WO | WO 99/04797 | 2/1999 |
| WO | WO 99/16419 | 4/1999 |
| WO | WO 99/24433 | 5/1999 |
| WO | WO 99/37347 | 7/1999 |
| WO | WO 99/37625 | 7/1999 |
| WO | WO 99/44664 | 9/1999 |
| WO | WO 99/55362 | 11/1999 |
| WO | WO 99/59710 | 11/1999 |
| WO | WO 99/64094 | 12/1999 |
| WO | WO 00/00176 | 1/2000 |
| WO | WO 00/00215 | 1/2000 |
| WO | WO 00/00244 | 1/2000 |
| WO | WO 00/19991 | 4/2000 |
| WO | WO 00/27359 | 5/2000 |
| WO | WO 00/27363 | 5/2000 |
| WO | WO 00/28979 | 5/2000 |
| WO | WO 00/29053 | 5/2000 |
| WO | WO 00/29167 | 5/2000 |
| WO | WO 00/35417 | 6/2000 |
| WO | WO 00/38618 | 7/2000 |
| WO | WO 00/44350 | 8/2000 |
| WO | WO 00/44730 | 8/2000 |
| WO | WO 00/47203 | 9/2000 |
| WO | WO 00/51491 | 9/2000 |
| WO | WO 00/64940 | 11/2000 |
| WO | WO 00/66084 | 11/2000 |
| WO | WO 00/66106 | 11/2000 |
| WO | WO 00/66206 | 11/2000 |
| WO | WO 00/72827 | 12/2000 |
| WO | WO 00/76673 | 12/2000 |
| WO | WO 01/05459 | 1/2001 |
| WO | WO 01/13957 | 3/2001 |
| WO | WO 01/17568 | 3/2001 |
| WO | WO 01/19528 | 3/2001 |
| WO | WO 01/29011 | 4/2001 |
| WO | WO 01/32144 | 5/2001 |
| WO | WO 01/41732 | 6/2001 |
| WO | WO 01/43801 | 6/2001 |
| WO | WO 01/95903 | 12/2001 |
| WO | WO 02/00198 | 1/2002 |
| WO | WO 02/24158 | 3/2002 |
| WO | WO 02/051466 | 7/2002 |
| WO | WO 02/051469 | 7/2002 |
| WO | WO 02/056866 | 7/2002 |
| WO | WO 02/083119 | 10/2002 |
| WO | WO 02/094234 | 11/2002 |
| WO | WO 02/098389 | 12/2002 |
| WO | WO 02/098496 | 12/2002 |
| WO | WO 02/102297 | 12/2002 |
| WO | WO 03/024456 | 3/2003 |
| WO | WO 03/037412 | 5/2003 |
| WO | WO 03/049535 | 6/2003 |

OTHER PUBLICATIONS

U.S. Appl. No. 11/964,630, filed Dec. 26, 2007, Hale et al.
U.S. Appl. No. 12/111,188, filed Apr. 28, 2008, Hale et al.
U.S. Appl. No. 12/117,737, filed May 8, 2008, Hale et al.
U.S. Appl. No. 12/211,247, filed Sep. 16, 2008, Sharma et al.
U.S. Appl. No. 12/211,554, filed Sep. 16, 2008, Sharma et al.
U.S. Appl. No. 12/211,628, filed Sep. 16, 2008, Lei et al.
U.S. Appl. No. 12/245,184, filed Oct. 3, 2008, Hale et al.
Office Action mailed Jan. 26, 2007 with respect to U.S. Appl. No. 10/057,198.
Office Action mailed Jul. 3, 2006 with respect to U.S. Appl. No. 10/057,198.
Office Action mailed Sep. 20, 2005 with respect to U.S. Appl. No. 10/057,198.
Office Action mailed Dec. 4, 2003 with respect to U.S. Appl. No. 10/057,198.
Office Action mailed Jan. 12, 2005 with respect to U.S. Appl. No. 10/057,197.
Office Action mailed Jun. 3, 2004 with respect to U.S. Appl. No. 10/057,197.
Office Action mailed Jun. 5, 2007 with respect to U.S. Appl. No. 10/057,197.
Office Action mailed Sep. 21, 2006 with respect to U.S. Appl. No. 10/057,197.
Office Action mailed Dec. 15, 2003 with respect to U.S. Appl. No. 10/057,197.
Office Action mailed Feb. 27, 2004 with respect to U.S. Appl. No. 10/146,080.
Office Action mailed Mar. 20, 2007 with respect to U.S. Appl. No. 10/146,080.
Office Action mailed Jun. 5, 2006 with respect to U.S. Appl. No. 10/146,080.
Office Action mailed Aug. 25, 2005 with respect to U.S. Appl. No. 10/146,080.
Office Action mailed Dec. 28, 2007 with respect to U.S. Appl. No. 10/146,080.
Office Action mailed Feb. 12, 2007 with respect to U.S. Appl. No. 10/146,086.
Office Action mailed Oct. 30, 2007 with respect to U.S. Appl. No. 10/146,086.
Office Action mailed Dec. 13, 2005 with respect to U.S. Appl. No. 10/146,086.
Office Action mailed Feb. 16, 2007 with respect to U.S. Appl. No. 10/146,088.
Office Action mailed Sep. 28, 2007 with respect to U.S. Appl. No. 10/146,088.
Office Action mailed Nov. 21, 2007 with respect to U.S. Appl. No. 10/146,088.
Office Action mailed Aug. 13, 2003 with respect to U.S. Appl. No. 10/153,313.
Office Action mailed Mar. 8, 2005 with respect to U.S. Appl. No. 10/718,982.
Anderson, M.E. (1982). "Recent Advances in Methodology and Concepts for Characterizing Inhalation Pharmacokinetic Parameters in Animals and Man," Drug Metabolism Reviews. 13(5):799-826.
Anonymous, (Jun. 1998) Guidance for Industry: Stability testing of drug substances and products, U.S. Department of Health and Human Services, FDA, CDER, CBER, pp. 1-110.
Bennett, R. L. et al. (1981). "Patient-Controlled Analgesia: A New Concept of Postoperative Pain Relief," Annual Surg. 195(6):700-705.

Benowitz (1994). "Individual Differences in Nicotine Kinetics and Metabolism in Humans," NIDA Research Monography, 2 pages.

BP: Chemicals Products-Barrier Resins (1999). located at <http://www.bp.com/chemicals/products/product.asp> (visited on Aug. 2, 2001), 8 pages.

Brand, P. et al. (Jun. 2000). "Total Deposition of Therapeutic Particles During Spontaneous and Controlled Inhalations," Journal of Pharmaceutical Sciences. 89(6):724-731.

Campbell, Fiona A. et al. (2001) "Are cannabinoids an effective and safe treatment option in the management of pain? A qualitative systemic review," BMJ, 323 pp. 1-6.

Carroll, M.E. et al. (1990), "Cocaine-Base Smoking in Rhesus Monkey: Reinforcing and Physiological Effects," Psychopharmacology (Berl) 102:443-450.

Cichewicz, Diana L. et al. (May 1999) "Enhancement of mu opioid antinociception by oral DELTA 9—tetrahydrocannabinol: Dose response analysis and receptor indentification" Journal of Pharmacology and Experimental Therapeutics vol. 289 (2): 859-867.

Clark, A. and Byron, P. (1986). "Dependence of Pulmonary Absorption Kinetics on Aerosol Particle Size," Z. Erkrank. 166:13-24.

Dallas, C. et al (1983). "A Small Animal Model for Direct Respiratory and Hemodynamic Measurements in Toxicokinetic Studies of Volatile Chemicals," Developments in the Science and Practice of Toxicology. Hayes, A. W. et al. eds., Elsevier Science Publishers, New York. pp. 419-422.

Darquenne, C. et al. (1997). "Aerosol Dispersion in Human Lung: Comparison Between Numerical Simulations and Experiments for Bolus Tests," American Physiological Society. 966-974.

Database Biosis "Online!" Biosciences Information Service, Philadelphia, PA 1979, Knight, V. et al., "Amantadine aerosol in humans", database accession No. PREV 198069035552 abstract, &Antimicrobial Agents and Chemotherapy 16(5);572-578.

Database Biosis "Online!" Biosciences Information Service, Philadelphia, PA 1979, Wilson. S.Z. et al., "Amatadine Aerosol Particle A.erosol Generation and Delivery to Man" Database accession No. PREV198069008137, abstract & Proceedings of the Society for Experimental Biology and Medicine 161(3):350-354.

Database WPI, Section CH, Week 198941, Derwent Publications Ltd., London, GB; AN 1989-297792 AP002230849 & JP 01 221313 (Nippon Create 1(K), Sep. 4, 1989, abstract.

Davies, C. N. et al. (May 1972). "Breathing of Half-Micron Aerosols," Journal of Applied Physiology. 32(5):591-600.

Dershwitz, M., M.D., et al. (Sep. 2000). "Pharmacokinetics and Pharmacodynamics of Inhaled versus Intravenous Morphine in Healthy Volunteers," Anesthesiology. 93(3): 619-628.

Drugs Approved by the FDA -Drug Name: Nicotrol Inhaler (2000) located at <http://www.centerwatch.com/patient/drugs/dru202.html> (Visited on Aug. 2, 2001), 2 pages.

Feynman, R.P. et al. (1964). "Chapter 32: Refractive Index of Dense Materials" The Feyman Lectures on Physics: Mainly Electromagnetism and Matter. Addison-Wesley: Publishing Company, Inc., Reading, Massachusetts: pp. 32-1-32-13.

Finlay, W. H. (2001). "The Mechanics of Inhaled Pharmaceutical Aerosols", Academic Press: San Diego Formula 2.39. pp. 3-14 (Table of Contents). pp. v-viii.

Gleeson, et al. (1982) "Chlorpromazine Hyperalgesia Antagonizes Clonidine Analgesia, but Enhances Morphine Analgesia in Rats Tested in a Hot-Water Tail-Flick Paradigm" Psychopharmacology vol. 78: 141-146.

Gonda, I. (1991). "Particle Deposition in the Human Respiratory Tract,"Chapter 176, The Lung: Scientific Foundations. Crystal R.G. and West, J.B. (eds.), Raven Publishers, New York. pp. 2289-2294.

Graves, D. A. et al. (1983). "Patient-Controlled Analgesia" Annals of Internal Medicine. 99:360-366.

Hamon, et al. (1987) "Opioid Receptors and Neuropeptides in the CNS in Rats Treated Chronically with Amoxapine and Amitriptyline" Neuropharmacology vol. 26 No. 6: 531-539.

Hatsukami D., et al. (May 1990) "A Method for Delivery of Precise Doses of Smoked Cocaine-Base to Human." Pharmacology Biochemistry & Behavior. 36(1):1-7.

Heyder, J. et al. (1986). "Deposition of Particles in the Human Respiratory Tract in the Size Range 0.005-15 μm," J. Aerosol Sci. 17(5):811-822.

Huizer, H. (1987). "Analytical Studies on Illicit Heron. V. Efficacy of Volitization During Heroin Smoking." Pharmaceutisch Weekblad Scientific Edition. 9(4):203-211.

Hurt, R. D., MD and Robertson, C. R., PhD, (Oct. 1998). "Prying Open the Door to the Tobacco Industry's Secrets About Nicotine: The Minnesota Tobacco Trial," JAMA 280(13):1173-1181.

Hwang, S. L. (Jun. 1999). "Artificial Nicotine Studied: R. J. Reynolds Seeks to Develop Drugs that Mimic Tobacco's Potent Effects on Brain," Wall Street Journal, 3 pages.

James, A.C. et al., (1991). "The Respiratory Tract Deposition Model Proposed by the ICRP Task Group," Radiation Protection Dosimetry, 38(1/3):159-165.

Kim, M. H. and Patel, D.V. (1994). "'BOP' As a Reagent for Mild and Efficient Preparation of Esters," Tet. Letters 35:5603-5606.

Lichtman, A. H. et al. (1996). "Inhalation Exposure to Volatilized Opioids Produces Antinociception in Mice," Journal of Pharmacology and Experimental Therapeutics. 279(1):69-76 XP-001118649.

Lichtman, A. H. et al. (2000). "Pharmacological Evaluation of Aerosolized Cannabinoids in Mice" European Journal of Pharmacology, vol. 399, No. 2-3: 141-149.

Lopez, K. (Jul. 1999). "UK Researcher Develops Nicotinic Drugs with R. J. Reynolds," located at <http://www.eurekalert.org/pub_releases/1999-07/UoKM-Urdn-260799.php> (visited on Oct. 1, 2002), 1 page.

Lynch, Mary E. (2001) "Antidepressants as analgesics: a review of randomized contolled trials" J. Psychiatry Neuroscience vol. 26: 30-36.

Magnusson et al. (2000) "The Involvement of Dopamine in Nociception: the role of D1 and D2 Receptors in the Dorsolateral Striatum." Brain Research vol. 855: 260-266.

Martin, B. R. and Lue, L. P. (May/Jun. 1989). "Pyrolysis and Volatilization of Cocaine," Journal of Analytical Toxicology 13:158-162.

Mattox, A.J. and Carroll, M.E. (1996). "Smoked Heroin Self-Administration in Rhesus Monkeys," Psychopharmacology 125:195-201.

McCormick, A.S.M., et al., "Bronchospasm During Inhalation of Nebulized Midazolam," British Journal of Anesthesia, vol. 80 (4), Apr. 1988, pp. 564-565 XP001119488.

McGee et al. (1979) "Phenotiazine Analgesia—Fact or Fantasy?" American Journal of Hospital Pharmacy vol. 36: 633-640.

Meng, Y. et al. (1997). "Inhalation Studies with Drugs of Abuse", NIDA Research Monograph 173:201-224.

Meng, Y. et al. (1999). "Pharmacological effects of methamphetamine and other stimulants via inhalation exposure," Drug and Alcohol Dependence. 53:111-120.

Pankow, J. (Mar. 2000). ACS Conference-San Francisco-Mar. 26, 2000. Chemistry of Tobacco Smoke. pp. 1-8.

Pankow, J. F. et al. (1997). "Conversion of Nicotine in Tobacco Smoke to Its Volatile and Available Free-Base Form through the Action of Gaseous Ammonia," Environ. Sci. Technol. 31:2428-2433.

Pfeiffer, Ronald (1982) "Drugs for pain in the elderly" Geriatrics vol. 37 No. 2: 67-76.

Poochikian, G. and Bertha, C.M. (2000). "Inhalation Drug Product Excipient Controls: Significance and Pitfalls," Resp. Drug Deliv. VII: 109-115.

Rapoport et al. (1997) CNS Drugs 7(1):37-46.

Schreiber et al. (1999) "The Atypical Neuroleptics Clozapine and Olanzapine Differ Regarding Their Antinociceptive Mechanisms and Potency" Pharmacology Biochemistry and Behavior vol. 64 No. 1: 75-80.

ScienceDaily Magazine, (Jul. 1999). "University of Kentucky Researcher Develops Nicotinic Drugs with R. J. Reynolds," located at <http://www.sciencedaily.com/releases/1999/07/990728073542.htm.> (visited on Sep. 23, 2002), 2 pages.

Seeman, J. et al. (1999). "The Form of Nicotine in Tobacco. Thermal Transfer of Nicotine and Nicotine Acid Salts to Nicotine in the Gas Phase," J. Agric. Food Chem. 47(12):5133-5145.

Sekine, H. and Nakahara, Y. (1987). "Abuse of Smoking Methamphetamine Mixed with Tobacco: 1. Inhalation Efficiency and Pyrolysis Products of Methamphetamine," Journal of Forensic Science 32(5):1271-1280.

Streitwieser, A. and Heathcock, C. H. eds., (1981). Introduction to Organic Chemistry. Second edition, Macmillan Publishing Co., Inc., New York, pp. ix-xvi. (Table of Contents).

Tsantilis, S. et al. (2001). "Sintering Time for Silica Particle Growth," Aerosol Science and Technology 34:237-246.

*Vapotronics, Inc.* (1998) located at http://www.vapotronics.com.au/banner.htm., 11 pages, (visited on Jun. 5, 2000).

Vaughan, N.P. (1990). "The Generation of Monodisperse Fibres of Caffeine" J. Aerosol Sci. 21(3):453-462.

Ward, M. E. MD, et al. (Dec. 1997). "Morphine Pharmacokinetics after Pulmonary Administration from a Novel Aerosol Delivery System," Clinical Pharmocology & Therapeutics 62(6):596-609.

Williams, S. (Feb. 1999). "Rhone-Poulenc Rorer Inc. and Targacept Inc. Announce Alliance to Develop New Drugs to Treat Alzheimer's and Parkinson's Diseases" located at http://www.rpr.rpna.com/ABOUT_RPR/pressrels/1999/990209-targa.html (last visited on Jan. 28, 2000) 1 page.

Wood, R.W. et al. (1996). "Methylecgonidine Coats the Crack Particle." Pharmacology Biochemistry & Behavior. 53(1):57-66.

Wood, R.W. et al. (1996). "Generation of Stable Test Atmospheres of Cocaine Base and Its Pyrolyzate, Methylecgonidine, and Demonstration of Their Biological Activity." Pharmacology Biochemistry & Behavior. 55(2):237-248.

U.S. Appl. No. 12/275,836, filed Nov. 21, 2008, Hale et al.

* cited by examiner

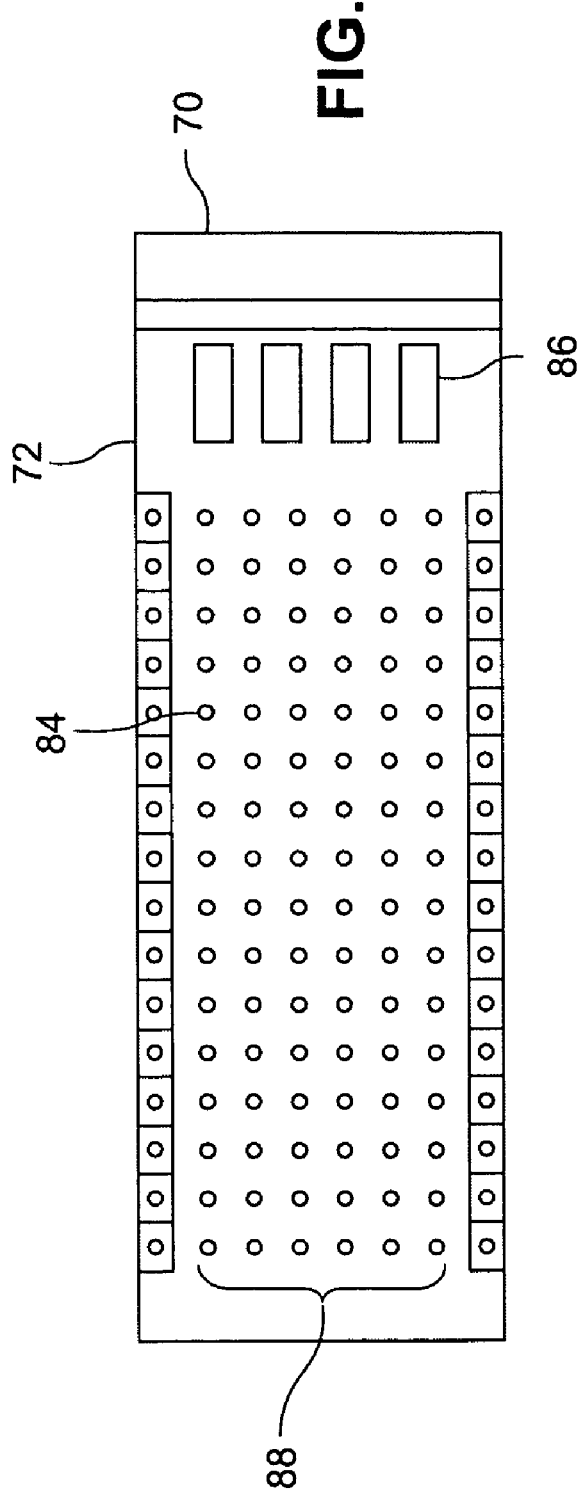
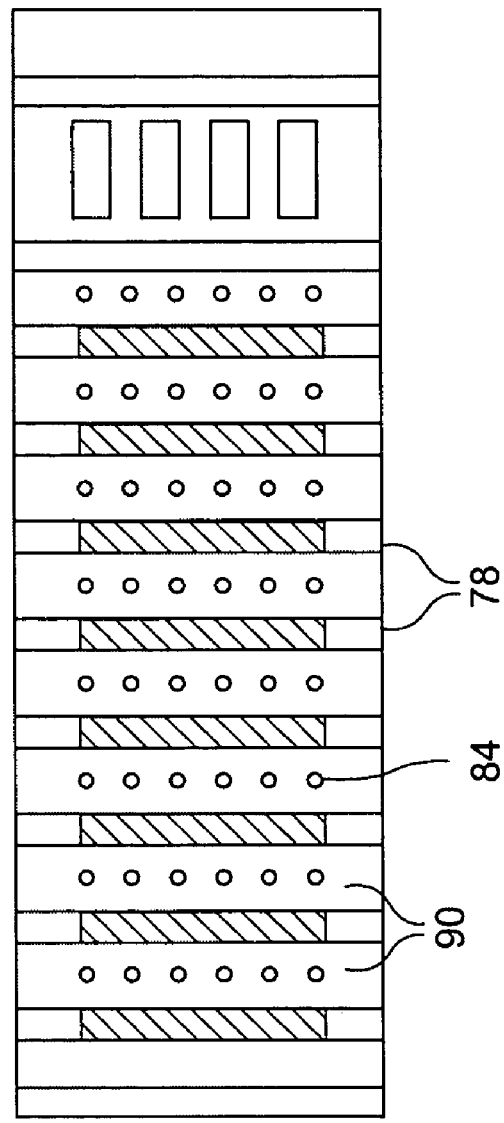

Before Heating
Flat Foil

During Heating
Flat Foil

Before Heating
Arched Foil

During Heating
Arched Foil

MULTIPLE DOSE CONDENSATION AEROSOL DEVICES AND METHODS OF FORMING CONDENSATION AEROSOLS

This disclosure relates to devices capable of entraining a substance into an airflow, to articles and methods employing such devices, and in particular to articles and methods of producing multiple doses of a condensation aerosol of a drug having high purity, high yield, characterized by a particle size distribution suitable for inhalation delivery, and which can be administered to a user during a single inhalation.

Pulmonary delivery is known as an effective way to administer physiologically active compounds to a patient for the treatment of diseases and disorders. Devices developed for pulmonary delivery generate an aerosol of a physiologically active compound that is inhaled by a patient where the compound can be used to treat conditions in a patient's respiratory tract and/or enter the patient's systemic circulation. Devices for generating aerosols of physiologically active compounds include nebulizers, pressurized metered-dose inhalers, and the dry powder inhalers. Nebulizers are based on atomization of liquid drug solutions, while pressurized metered-dose inhalers and dry powder inhalers are based on suspension and dispersion of dry powder in an airflow and/or propellant.

Aerosols for inhalation of physiologically active compounds can also be formed by vaporizing a substance to produce a condensation aerosol comprising the active compounds in an airflow. A condensation aerosol is formed when a gas phase substance formed from vaporization condenses or reacts to form particulates (also called particles herein) in the air or a gas. Examples of devices and methods employing vaporization methods to produce condensation aerosols are disclosed in U.S. Pat. Nos. 6,682,716; 6,737,042; 6,716,415; 6,716,416; 6,740,307; 6,740,308; 6,737,043; 6,740,309; and 6,716,417, each of which is incorporated herein by reference.

It can be desirable that an inhalation device be capable of delivering multiple doses of a physiologically active compound and that each dose comprising the active compound be administered to a patient during a single inhalation. A dose refers to the amount of a substance released during one activation of an inhalation device. A dose can comprise, for example, a therapeutically effective amount of a physiologically active compound. Furthermore, treatment regimens can require that each of the multiple doses delivered to a patient comprise a controlled amount of a physiologically active compound, and that the active compound administered exhibit high purity and be free of byproducts, e.g., excipients. Optimal delivery of a dose to a patient's respiratory tract, and in particular to a patient's lungs, can also be facilitated by the aerosol having a mass median aerodynamic diameter of less than about 4 µm. Furthermore, practical considerations make it desirable that a substantial amount of each dose contained in the device, form an aerosol, be emitted from the device, and be inhaled by the patient.

When a condensation aerosol is formed in an airflow, a certain portion of the aerosol can deposit on downstream physical features such as the side walls of the airway defining the airflow, the mouthpiece of the device, or other structures and thereby reduce the amount of active compound emitted by the device and available for administration. In multiple dose devices, packaging the multiple doses within a common airway can be attractive for producing low cost and compact products. However, in multiple dose devices, where the multiple doses are disposed on surfaces within an airflow, a certain amount of an aerosol particles formed by vaporizing an upstream dose, can deposit onto downstream surfaces comprising unvaporized compound. Not only can the deposition on unvaporized doses reduce the amount of active compound emitted from the device, but in addition, the deposition can change the amount of active compound forming subsequent doses. Thus, particularly where a device includes a large number of multiple doses, the latter doses can comprise a variable and uncontrolled amount of an active compound.

For many treatment regimens, the ability to deliver a dose comprising a precise, consistent, and reproducible amount of a physiologically active compound can impact the therapeutic efficacy of the treatment regimens, and in some cases, such a capability can also enable new therapies. Thus, there is a need for inhalation devices and methods of producing a condensation aerosol that can repeatedly deliver precise, reproducible and/or controlled amounts of a physiologically active substance.

Certain embodiments include devices for entraining a substance within an airflow comprising an airway with an inlet, and an outlet; at least one support disposed within the airway; the substance disposed on the at least one support; and a mechanism configured to release the substance from the at least one support; wherein an airflow passing from the inlet to the outlet is directed to the at least one support such that the substance is entrained in the airflow when released from the support.

Certain embodiments include electrically resistive heating elements comprising a metal foil for vaporizing a substance disposed thereon to produce a condensation aerosol comprising the substance.

Certain embodiments include devices for delivering a condensation aerosol to a subject comprising a dispensing unit and a separable cartridge. In certain embodiments, the dispensing unit comprises a first housing comprising a receptacle for a separable cartridge; a controller for controlling vaporization of the substance; and a power source. In certain embodiments, the separable cartridge comprises a second housing; an airway contained within the housing having an inlet, and an outlet; a mouthpiece coupled to the outlet; an air bypass hole coupled to the outlet; at least one electrically resistive heating element disposed within the airway; a substance disposed on the at least one heating element; and an actuation mechanism configured to transfer energy from the power source to the at least one heating element; wherein an airflow from the inlet to the outlet of the airway causes the substance to vaporize and condense in the airflow to form a condensation aerosol.

Certain embodiments include methods of entraining a vaporized substance or aerosol particles into an airflow, methods of producing a condensation aerosol, and methods of administering a substance to a subject using the devices disclosed herein. For purposes herein, "entrain" or "entraining" means to direct, lift, draw in or along, inject, transport, carry, or suspend a vaporized substance or aerosol particle into an airflow.

Other embodiments will be apparent to those skilled in the art from consideration and practice of the invention disclosed herein. It is intended that the specification and examples be considered as exemplary only.

It is to be understood that both the foregoing general description and the following detailed description are exemplary and explanatory only and are not restrictive of certain embodiments, as claimed.

DESCRIPTION OF THE DRAWINGS

FIGS. 6A and 6B show views of a structure separating the first airway and the second airway according to certain embodiments.

DESCRIPTION OF VARIOUS EMBODIMENTS

Unless otherwise indicated, all numbers expressing quantities and conditions, and so forth used in the specification and claims are to be understood as being modified in all instances by the term "about."

In this application, the use of the singular includes the plural unless specifically stated otherwise. In this application, the use of "or" means "and/or" unless stated otherwise. Furthermore, the use of the term "including," as well as other forms, such as "includes" and "included," is not limiting.

Condensation aerosols can be formed when a gaseous substance condenses or reacts to form particulates in air or a gas. A gaseous substance can be produced when a solid or liquid substance is thermally sublimed or vaporized. Vaporization refers to a phase transition in which a substance changes from a solid or liquid state into a gaseous state. Sublimation refers to a phase transition in which a substance passes directly from a solid state to a gaseous state.

Upon entering an airflow, a gaseous substance can cool and, at least in part depending on the temperature of the airflow, can condense to form an aerosol particle. Condensation aerosol particles not sufficiently entrained within the airflow have a greater probability of falling out of the airflow to deposit on a downstream surface.

Figure 1A:
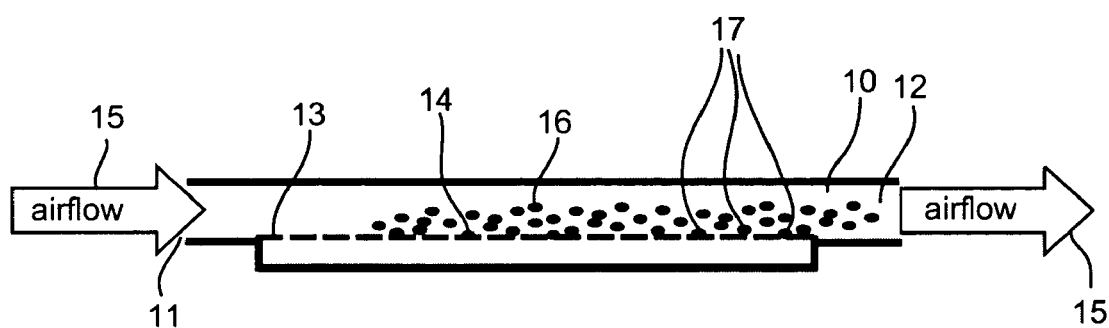
FIG. 1A is a schematic illustration showing deposition of a substance on downstream surfaces.

Inefficient entrainment of particulates within an airflow and subsequent deposition of the particulates on downstream surfaces is shown in FIG. 1A. FIG. 1A shows an airway 10 having an inlet 11 and an outlet 12. A plurality of supports 13 are located on one side of airway 10. Plurality of supports 13 include support 14 and downstream supports 17. A substance can be disposed, for example, on support 14, and an airflow 15 established in airway 10 such that plurality of supports 13 including support 14 are disposed in airflow 15. When the substance disposed on support 14 is released from support 14 by, for example, vaporization, the substance can form condensation aerosol particles 16 in airflow 15. As shown, when the aerosol particles are not fully entrained within airflow 15, condensation aerosol particles 16 so formed can deposit on downstream supports 17.

Figure 1B:
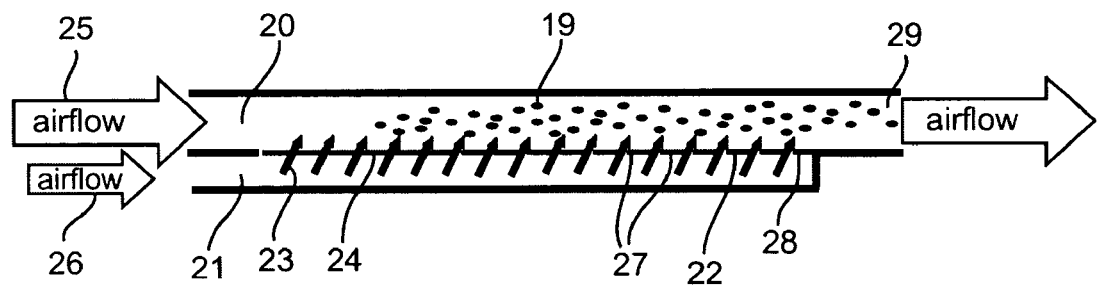
FIG. 1B is a schematic illustration showing the use of an airflow through a plurality of holes to entrain a substance into an airflow and thereby minimize deposition of the substance on downstream surfaces according to certain embodiments.

A schematic illustration of a device for entraining a particulate, and in particular an aerosol-forming gas phase substance, within an airflow is shown in FIG. 1B. FIG. 1B shows a first airway 20 and a second airway 21 separated by a structure 22. Structure 22 comprises a plurality of holes fluidly connecting first airway 20 and second airway 21. A plurality of supports 28 including upstream support 24, and downstream supports 27 are disposed on the surface of structure 22 within first airway 20. As in FIG. 1A, a substance can be disposed, for example, on upstream support 24. A first airflow 25 can be established in first airway 20, and a second airflow 26 can be established in second airway 21 such that second airflow 26 passes from second airway 21 to first airway 20 through the plurality of holes as indicated by the upward pointing arrows 23. Upon passing through the plurality of hole, second airflow 26 can provide a flow of air directed toward plurality of supports 28, including upstream support 24 and directed toward airflow 25. The flow of air 23 directed toward airflow 25 can act to lift a substance vaporized from upstream support 24 to form condensation aerosol particles 19 comprising the substance, and entrain the condensation particles within first airflow 25. Entrainment of condensation particles 19 within first airflow 25 will reduce the likelihood that the condensation particles 19 will become deposited on the downstream surfaces 27. As shown in FIG. 1B, by entraining the condensation particles near the center of first airflow 25, more of the condensation particles can be emitted as an aerosol from the outlet 29 of the device and be available, for example, for administration to a subject by inhalation.

Figure 2A:
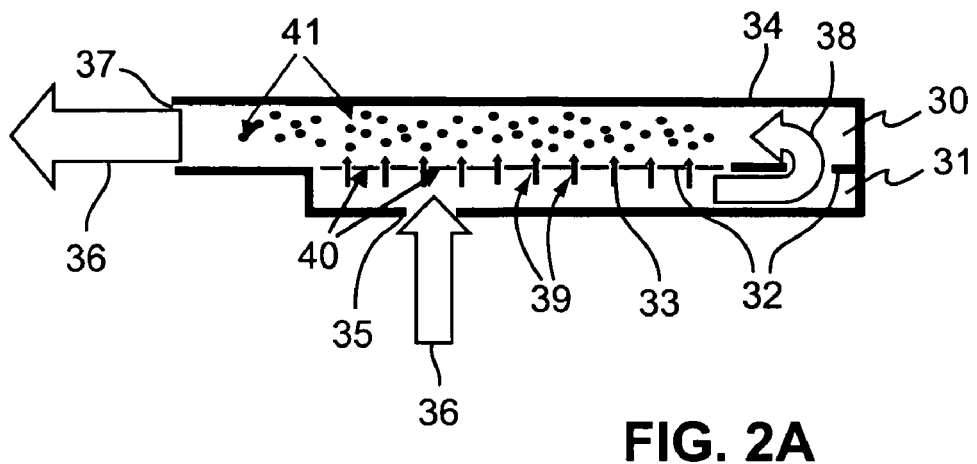
FIGS. 2A-2F are schematic illustrations showing examples of airflow routing in a device for entraining a condensation aerosol particle into an airflow according to certain embodiments.

Another embodiment of a device for entraining a substance, and in particular, a gas phase substance, within an airflow to form a condensation aerosol is schematically illustrated in FIG. 2A. FIG. 2A shows another scheme for routing an airflow through a plurality of holes and across a surface of a structure. FIG. 2A shows a device having a first airway 30, a second airway 31, and a structure 32 separating first airway 30 and second airway 31. Although structure 32 is shown as comprising two parts, e.g., as indicated by the thick and thin lines, structure 32 can comprise one part or multiple parts. Structure 32 includes a plurality of holes 39 which fluidly connect first airway 30 and second airway 31. First airway 30 and second airway 31 are further defined by housing 34. Housing 34 includes an air intake 35 to allow airflow 36 to enter second airway 31, and an air outlet 37 to allow airflow 36 to exit the device. As shown in FIG. 2A, first airway 30 and second airway 31 are further fluidly connected through holes and/or slots dimensioned to permit a greater, less than, or equal portion 38 of airflow 36 to pass into first airway 30, compared to the portion of airflow the airflow that passes through plurality of holes 39. The relative amounts of airflow to each airway can be altered to suit the desired purpose. In the same manner as described for FIG. 1B, the airflow through plurality of holes 39 as indicated by small arrows 33, entrains the vaporized substance and the condensation particles 41 formed by condensation of the vaporized substance released from the plurality of supports 40 disposed on structure 32 within airflow 36. Entrainment of condensation particles 41 within airflow 36 reduces deposition of the condensation particles 41 on downstream surfaces.

Figure 2B:
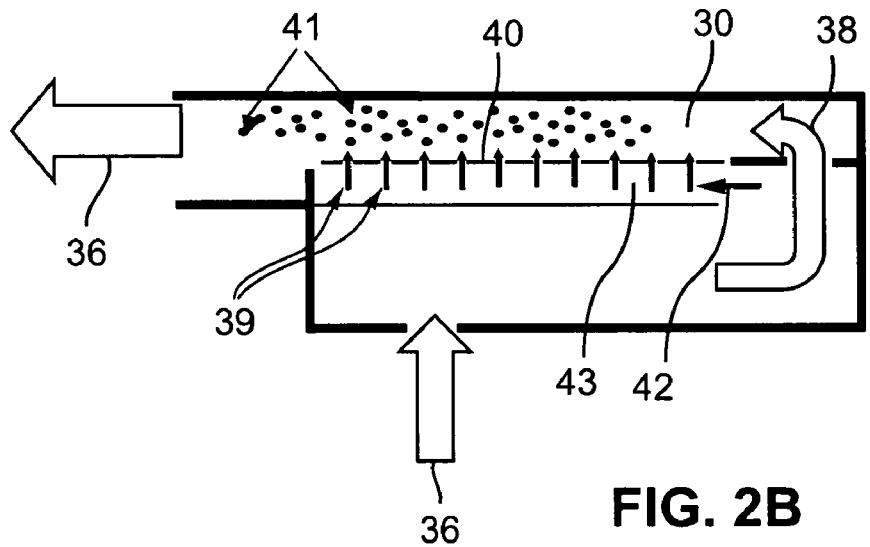

Another embodiment of a device for entraining a substance or condensation particles within an airflow is shown in FIG. 2B. FIG. 2B shows a device similar to that of FIG. 2A wherein a second airflow 42, which is a portion of airflow 36, enters a third airway 43. Second airflow 42 can then pass through the plurality of holes 39 to provide an airflow directed toward a plurality of supports 40 and the first airway 30. The condensation particles 41 formed by vaporizing a substance disposed on the supports becomes entrained in airflow 36, which includes airflows 38 and 42.

Figure 2C:
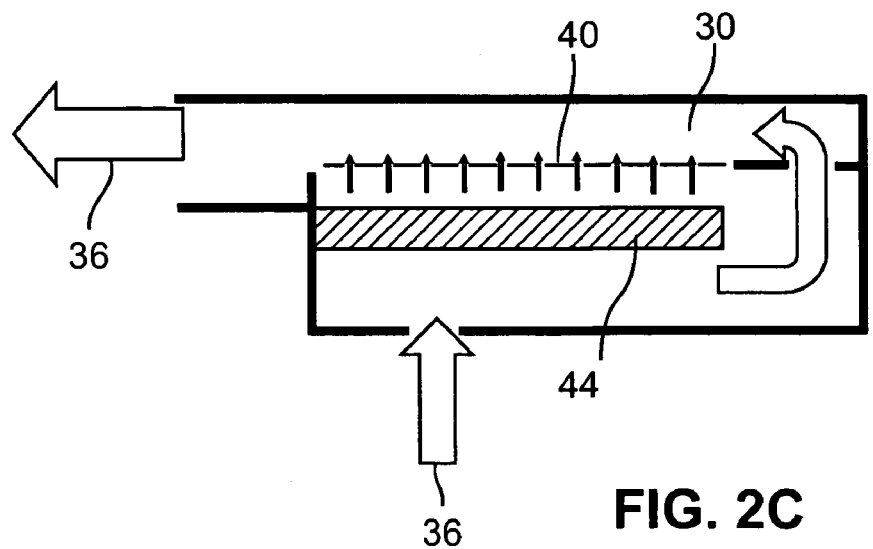

In another embodiment, as shown in FIG. 2C, a portion of first airflow 36 is directed through a porous element 44. On passing through porous element 44, this portion of airflow passes between supports 40 and directs the airflow toward first airway 30. Porous element 44 can be fabricated from any material and have any pore size capable of distributing an appropriate portion of the air entering the device through the plurality of holes forming porous element 44. For example, in certain embodiments, porous element 44 can be an open cell foam, a mesh, a fibrous material, a glass frit, a ceramic filter, a microporous element, and the like.

How effectively a substance is entrained within an airflow can at least in part depend on the proportion of rate of airflow across the surface of a support, $R_1$ to the rate of airflow through the plurality of openings, $R_2$. The appropriate proportion $R_1:R_2$ for effectively entraining a substance within an airflow can depend on a number of factors such as the airflow velocity and the distance of the support from the center of the airflow. In certain embodiments, $R_1:R_2$ can range from 80:20 to 20:80 and in other embodiments can range from 60:40 to 40:60. The proportion $R_1:R_2$ can be established by the relative areas of the holes through which the first an second airflows pass. For example, referring to FIG. 2A, a proportion of 60:40 means that the relative area of hole/slot through which airflow 38 passes is 60 and the relative area of the plurality of holes 39 is 40.

Figure 2D:
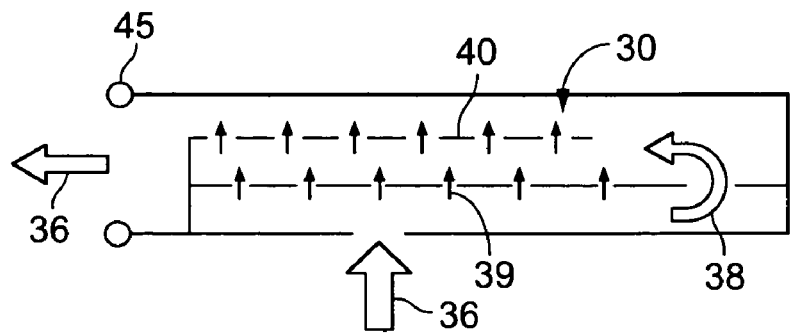

Another embodiment of a device for entraining a substance in an airflow is shown in FIG. 2D. FIG. 2D shows airflow 36 entering the device. One portion of airflow 36 passes through a plurality of holes 39 and across a plurality of supports 40. A second portion of airflow 36 is diverted around the plurality of holes (shown on FIG. 2D as 38). The airflow portion that goes through the plurality of holes 39 and second airflow portion 38 recombine in first airway 30 and pass through mouthpiece 45 to exit the device.

In the embodiments shown in FIGS. 1B and 2A-D by introducing air from below the supports redeposition of the vaporized substance or aerosol condensation particles is minimized.

Figure 2E:
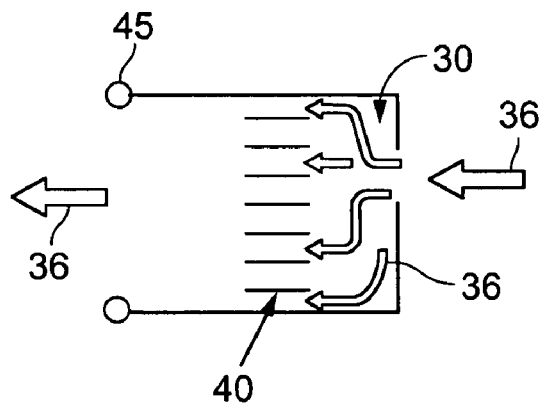
Figure 2F:
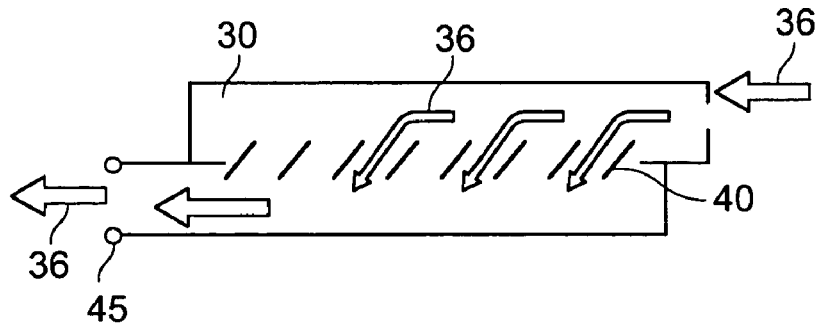

Different arrangements of the supports with respect to the airflow through the device are shown in FIGS. 2E and 2F. In FIG. 2E, airflow 36 enters first airway 30. Airflow 36 is routed over a plurality of supports 40 and recombines to pass through mouthpiece 45 to exit the device. In FIG. 2F, airflow 36 entering first airway 30 passes over plurality of supports 40 to pass through mouthpiece 45 to exit the device.

Figure 3:
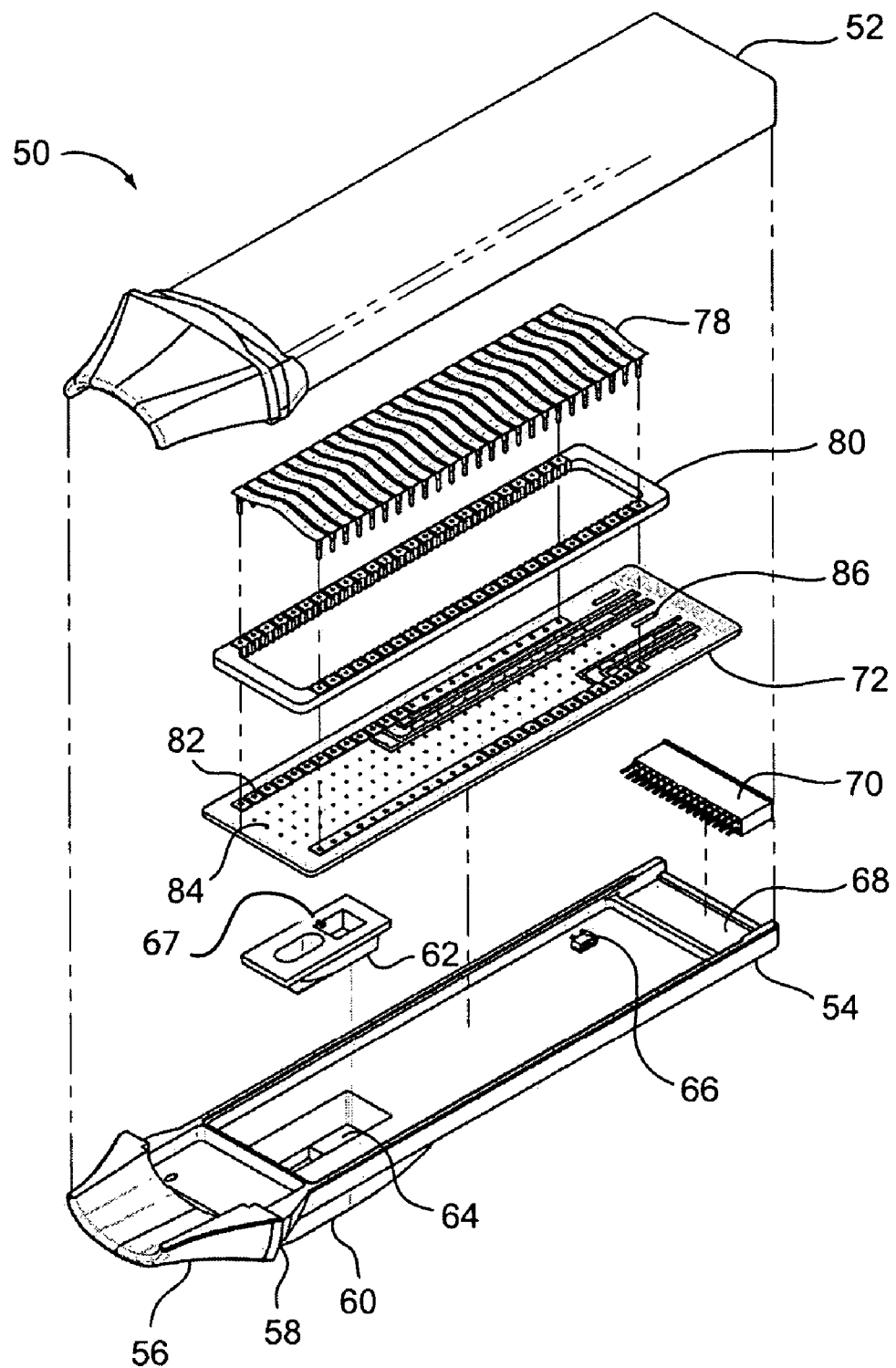
FIG. 3 is an isometric diagram of a separable cartridge for an electric multi-dose condensation aerosol delivery device.
Figure 5:
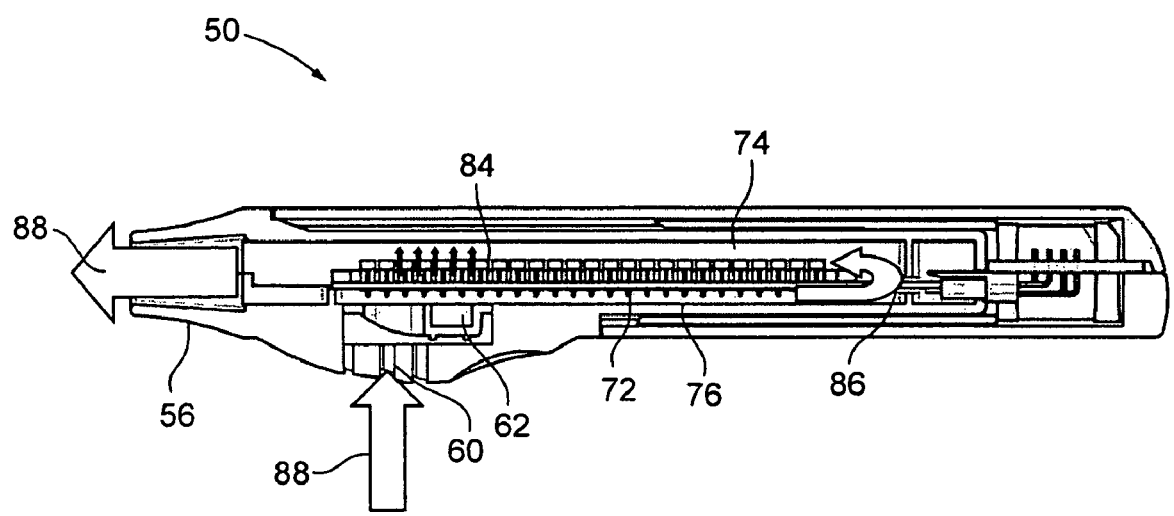
FIG. 5 is a schematic cross-sectional illustration of a separable cartridge for an electric multi-dose condensation aerosol delivery device showing the routing of the airflow according to certain embodiments.

The concepts underlying the exemplary devices illustrated in FIGS. 1B, 2A-2F can be applied to devices for administering a condensation aerosol to a subject. A subject includes mammals and humans. A cartridge for administering multiple doses of a condensation aerosol to a subject which employs airflow through a plurality of holes to facilitate entrainment of a substance released from a support within an airflow is illustrated in FIG. 3. An exploded assembly view of such a cartridge is shown in FIG. 3 as part 50. A cross-sectional view of an assembled cartridge is also illustrated in FIG. 5.

FIG. 3 shows an isometric assembly view of a cartridge capable of producing multiple doses of a substance for pulmonary administration. The cartridge 50 illustrated in FIG. 3 comprises a first shell 52 and a second shell 54 which can be coupled to form a housing. When assembled, one end of first shell 52 and second shell 54 form a mouthpiece 56 for insertion in a subject's mouth. An air bypass hole 58 is located adjacent to mouthpiece 56 in second shell 54 to enable air to enter mouthpiece 56 when the rate of airflow generated by inhalation exceeds the rate of airflow controlled by an air inlet valve 62 entering the cartridge. The air inlet valve 62 can assist in minimizing any air flow variation from user to user. The rate of airflow in the housing can impact particle size and thus controlling air flow variation allows for more control over the particle size generated. The air bypass hole 58 allows for flexibility in that it allows the user to breath at a comfortable rate without upsetting the amount of air flow that moves through the housing and across the surface of the supports. For example, a person typically inhales at a flow rate ranging from 30 L/min to 100 L/min. A device, however, may have a flow rate of 6 L/min, which refers to the volume of air per time entering the device, being directed across the surface of the supports and emitted from the device, the excess airflow from the person will enter bypass hole 58. Second shell 54 further comprises an air intake 60 (partially hidden). Air intake 60 includes air inlet valve 62 that fits into receptacle 64 of second shell 54. As discussed above, air inlet valve 62 controls the airflow rate of the cartridge and can be any valve that can control the amount of air entering the device during a single inhalation by a user. Examples of appropriate valves include flapper valves (a flexible value that bends in response to a pressure differential), umbrella valves, reed valves, or flapping valves that bend in response to a pressure differential, and the like. The purpose of air inlet valve 62 is to control the amount of air entering the cartridge regardless of the total airflow rate during and among inhalations. The total airflow rate includes the airflow rate through air intake 60 and air inlet valve 62, and the airflow rate through air bypass hole 58.

Figure 4:
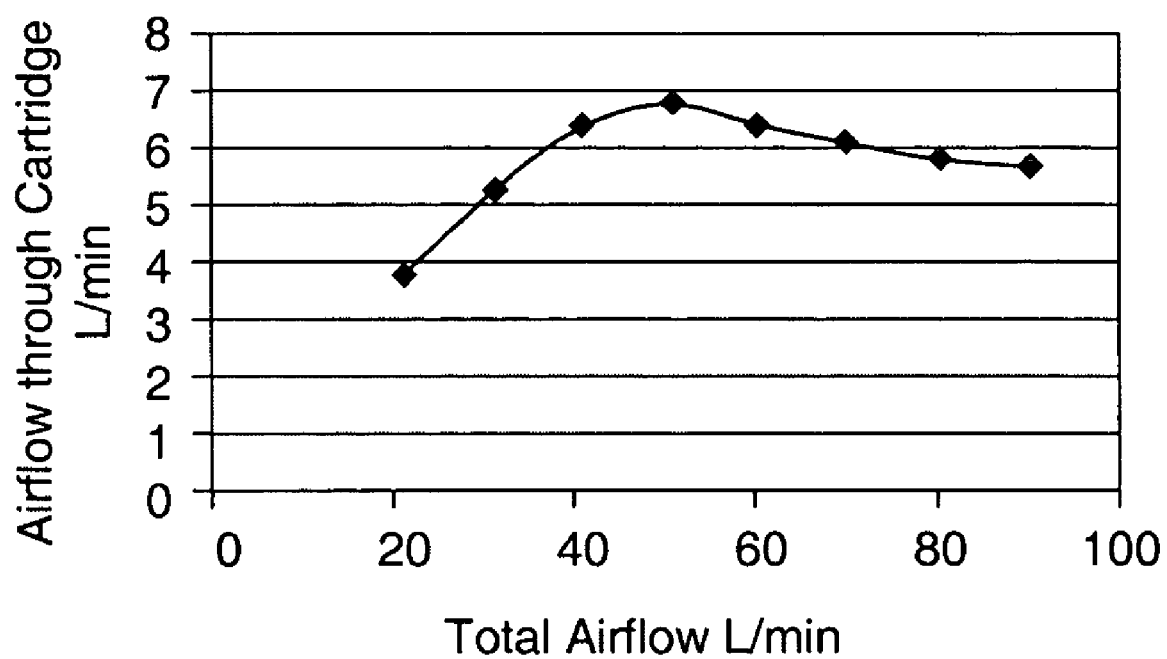
FIG. 4 shows the airflow rate in the airway for different total airflow rates for a cartridge.

FIG. 4 demonstrates that a simple flap valve can be used to control the airflow rate through the cartridge to about 6 L/min for total inhalation ranging from 20 L/min to 90 L/min. To generate the results presented in FIG. 4, a cartridge was fitted with a flap valve and the airflow rate through the cartridge for various total airflow rates was measured. Thus, by using air inlet valve 62, the airflow rate through the cartridge can be relatively independent of the airflow rate generated by an inhalation. As disclosed herein, flow control can be used to control the particle size and particle size distribution of the condensation aerosol emitted from the device. However, particle size and particle size distribution can be impacted by a number of additional factors including, for example, the substance, the vaporization temperature of the substance, the temperature of the airflow and the cross-sectional air of the airway. Thus, the airflow rate can be one of several parameters to be adjusted to produce a desired average particle size and particle size distribution. In certain embodiments, air control valve 62 can be designed to control the airflow through the cartridge between 4 L/min and 8 L/min. In certain embodiments, an airflow control valve can be activated electronically such that a signal provide by a transducer located within the airway can control the position of the valve, or passively, such as, for example, by a pressure differential between the airway and the exterior of the device. Additionally, the cross-sectional area of the airway can be adjusted to produce a desired average particle size and particle size distribution. In certain embodiments the cross-section area of the airway ranges from 0.5 cm$^2$ to 3 cm$^2$.

As shown in FIG. 3, second shell 54 further includes a breath actuation mechanism 67. Breath actuation mechanism 67 is electrically coupled to a remotely located controller (not shown) and can send a signal to the controller that interprets the data and activates the generation of a condensation aerosol when a certain pre-established airflow velocity is sensed. Breath actuation mechanism 67 can be, for example, a thermistor, which senses temperature in response to airflow. First shell 52 and second shell 54 also include a receptacle 68 for retaining electrical connector 70. In addition, there can be a counter 66, which identifies the number of supports that have not been actuated in that they have not been heated yet to vaporize the substance contained thereon.

When cartridge 50 is assembled, a structure 72 separates a first airway and a second airway. First airway 74 and second airway 76 are formed by structure 72 and the opposing inner walls of first and second shells 52, 54, respectively, as shown in the cross-sectional view of the assembled cartridge illustrated in FIG. 5. As shown in FIG. 3, structure 72 is a printed circuit board enabling electrical connection between connector 70 and a plurality of electrically resistive heating elements 78. Heating elements 78 are mounted on spacer 80 and soldered to interconnection lands 82 disposed on structure 72. Spacer 80 can be a thermally insulating material such as, for example, a printed circuit board material.

As shown in FIG. 3, structure 72 includes a plurality of holes 84 extending over most of the surface of structure 72. Each of the holes 84 extends through the thickness of structure 72. Structure 72 also includes a set of slots 86 near the end of structure 72 on which connector 70 is mounted. The number and dimensions of plurality of holes 84 and set of slots 86 determine the relative proportion of air which flows through the plurality of holes 84 and set of slots 86 when a subject inhales on mouthpiece 56. As shown in FIG. 5, when a subject inhales on mouthpiece 56 of cartridge 50, an airflow 88 is generated such that air enters air intake 60, the flow of air entering the device is controlled by air inlet valve 62 to enter second airway 76. A first portion of airflow passes from second airway 76 through a set of slots 86 into first airway 74 to be inhaled by a subject. At the same time, a second portion of airflow passes through plurality of holes 84 and enters first airway 74 to be inhaled by the subject. The airflows passing through the plurality of holes 84 and the set of slots 86 combine to pass through mouthpiece 56 to exit the device.

A top view showing the positioning of plurality of holes 84 and set of slots 86 with respect to plurality of supports 78 is shown in FIGS. 6A and 6B. FIG. 6A shows structure 72 comprising connector 70, set of slots 86 and plurality of holes 84. Set of slots 86 are shown as rectangular slots. However, set of slots 86 can have any number of openings, shapes, and/or dimensions as appropriate to cause a vaporized substance to become entrained within the airflow so as to form a condensation aerosol that exhibits appropriate properties for inhalation administration. Plurality of holes 84 is shown as comprising a regular array of round openings. However, plurality of holes 84 can have any number of openings, shapes, and/or dimensions as appropriate to cause a vaporized substance and condensation aerosol particles to be entrained within the airflow to form a condensation aerosol exhibiting appropriate properties for inhalation administration. For example, each row of holes 88 can instead be a narrow slot. Plurality of holes 84 can also be placed in a different arrangement over the surface of structure 72.

As shown in FIG. 6B, in certain embodiments, holes 84 can be positioned beneath gaps 90 between adjacent heating elements 78. Air flowing from holes 84 through gaps 90 can direct a substance released from supports 78 into an airflow. In certain embodiments, at least some of the plurality of holes 84 can be located beneath at least some of the supports 78.

Figure 7:
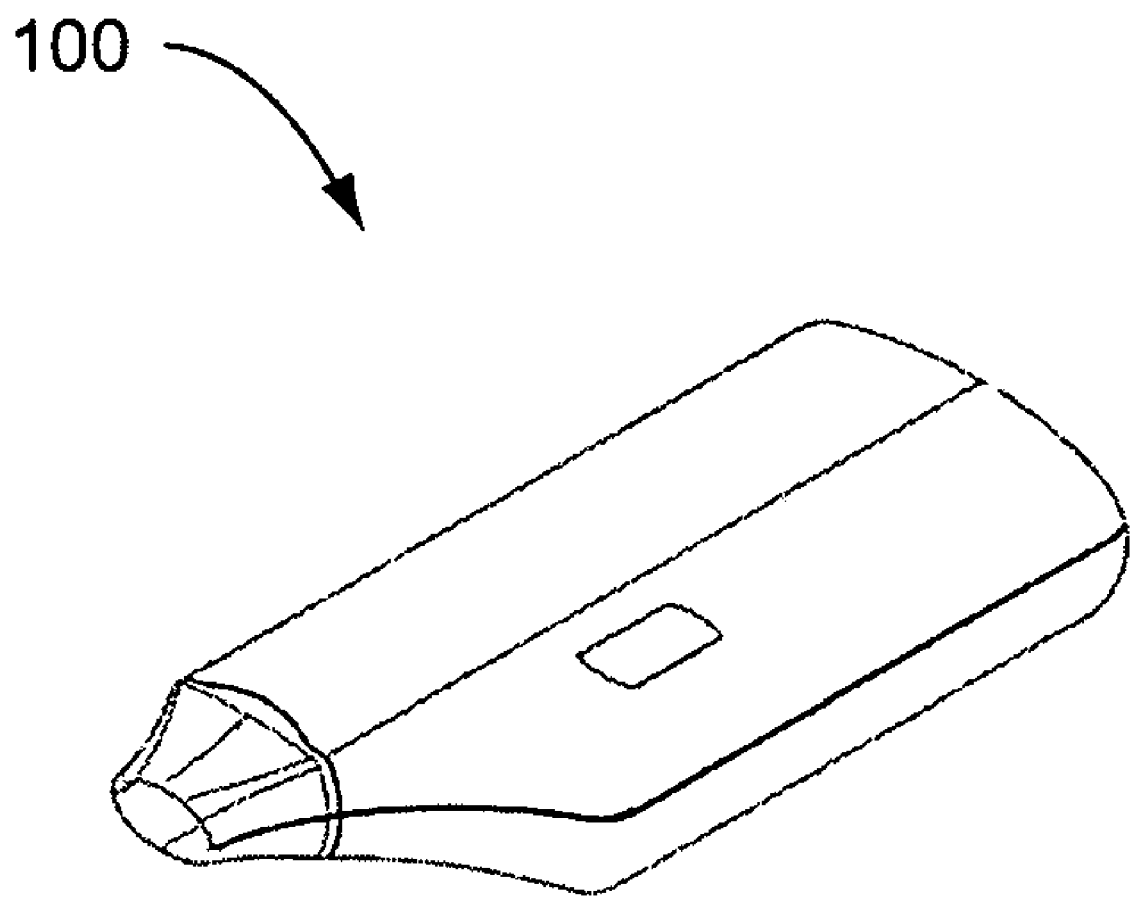
FIG. 7 is a isometric view of an electric multi-dose condensation aerosol delivery device.
Figure 8:
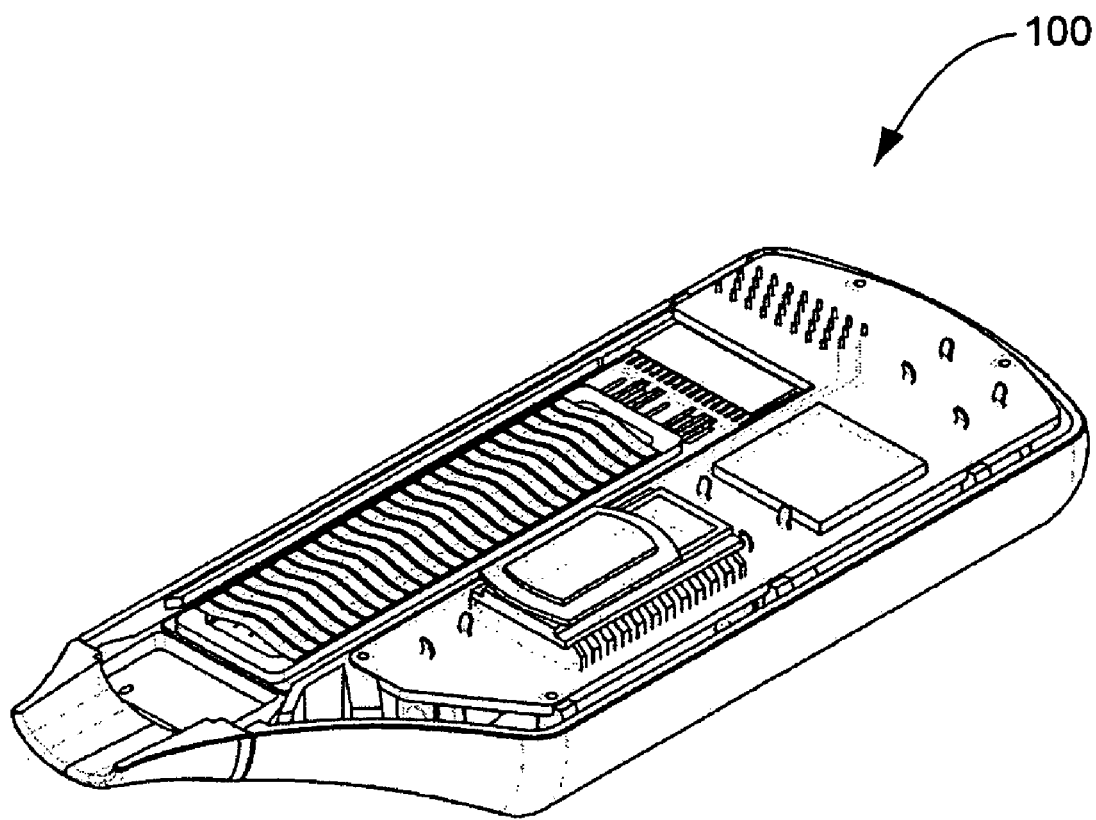
FIG. 8 is a cut-away isometric view of a portion of an electric multi-dose condensation aerosol delivery device.
Figure 9:
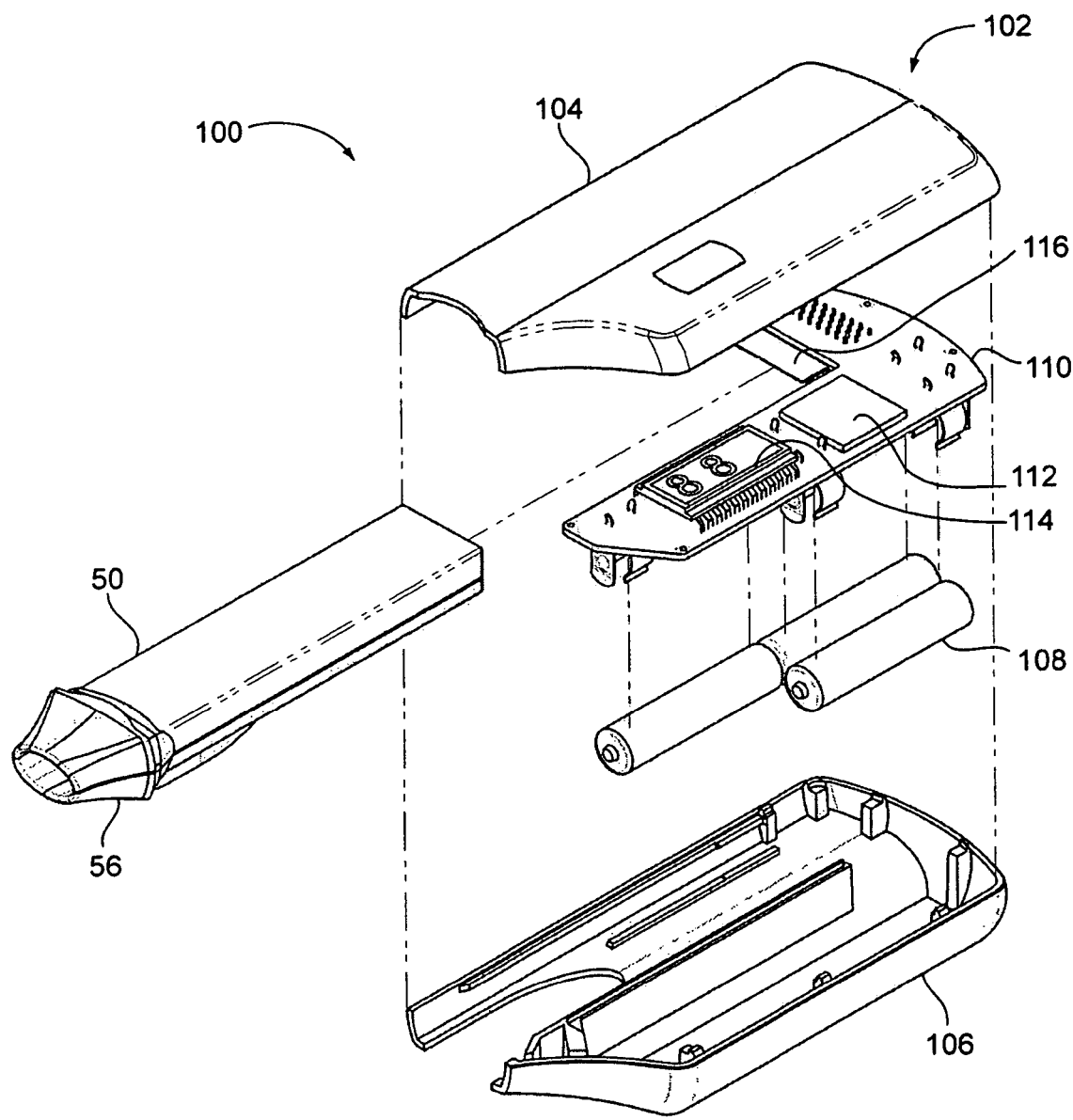
FIG. 9 is an isometric view of a dispensing unit for an electric multi-dose condensation aerosol delivery device.

A cartridge as described in FIGS. 2-6 can be used in a condensation aerosol delivery device for the administration of a physiologically active substance to a subject. A solid view of an exemplary condensation aerosol delivery device 100 according to the disclosure is shown in FIG. 7. An isometric view with the top of the device and the cartridge removed is shown in FIG. 8, and an exploded isometric view of the condensation aerosol delivery device 100 is shown in FIG. 9. Referring to FIG. 9, the condensation aerosol delivery device 100 includes cartridge 50 and a dispensing unit 102. As shown in FIG. 9 cartridge 50 can be a separable unit. In certain embodiments, cartridge 50 can be an integral component of dispensing unit 102. Dispensing unit 102 includes a first shell 104 and a second shell 106 which can be assembled to form the housing of dispensing unit 102. As shown in FIG. 9, dispensing unit 102 further includes a battery power source 108, and a printed circuit board 110 incorporating a microprocessor controller 112, a display 114, and a connector 116 for connecting the dispensing unit with the cartridge and which also connects to controller 112 and power source 108 comprising three AAA batteries to cartridge 50.

To deliver a condensation aerosol to a subject, the subject places mouthpiece 56 of condensation aerosol delivery device 100 into his or her mouth. The subject then inhales on mouthpiece 56 to generate an airflow as described herein. When a certain minimum airflow or a rate in change in airflow is sensed, the device is triggered. A signal from the airflow sensor is sent to the controller to cause the battery power source to connect to at least one support. As described herein, the supports can be, for example, electrically resistive heating elements. Heat produced by the electrically resistive heating element thermally vaporizes the substance disposed thereon.

The vaporized substance condenses in the airflow to form condensation particles and hence, a condensation aerosol. As described herein, the airflow passing from beneath the heating element causes the substance vaporized from the heating element or the condensed aerosol particles to become entrained in the airflow as opposed to depositing on other supports prior to passing through the cartridge. The aerosol upon passing through the cartridge is subsequently inhaled by the subject. Activation of the condensation aerosol delivery device, generation of the condensation aerosol, and inhalation of the condensation aerosol can occur in a single breath. The inhaled condensation aerosol then enters the subject's respiratory tract where the condensation aerosol comprising the active substance can be deposited in the respiratory tract, and in particular the pulmonary alveoli, of the subject.

A device for generating a condensation aerosol can include at least one support and in certain embodiments, for example, as shown in FIGS. 2-5 and 8, can include a plurality of supports. The supports can provide a surface and/or structure on which a substance to be released into an airflow can be disposed. In certain embodiments, the supports can be located at a side of the airway, for example on the surface of the structure, or can be located toward, near, or in the center of the airway. The shape and dimensions of the supports, and the material or materials forming the supports can be chosen to facilitate release of a substance disposed on the supports upon the application of energy, to minimize degradation of the substance during release, to cause rapid heating of the substance disposed thereon and/or to minimize the amount of energy used to release the substance.

Selection of the appropriate material for forming the support can also, at least in part, be determined by the source of energy used to release the substance from the support. For example, the source of energy used to release the substance can be mechanical, acoustic, radiation such as microwave, radio frequency or optical, and/or thermal. When the applied energy is absorbed directly by the substance, the support can be non-thermally conductive. For example, an optical source can be used to ablate and/or vaporize a substance disposed on a support. Alternatively, in certain embodiments, it can be more efficient or practical to heat a thermally conductive support which transfers thermal energy to the substance disposed thereon to release the substance from the support. In such embodiments, the support can be a thermally conductive material such as a metal, a metal alloy, a metal composite having more than one layer and/or composition, graphite, or the like. For example, in certain embodiments the metal can be stainless steel, copper, nickel, aluminum, gold, or silver, and can be plated with one or more of the foregoing materials or other metals. In some embodiments, the thickness of the plating of a metal layer on the metal can be within the range of between 0.001 μm to 3 μm and in other embodiments. In some embodiments, the support can be a semi-conducting material.

In certain embodiments, for example, where the condensation aerosol delivery device is designed for portable use with a battery power source, efficient energy use can be desirable. Minimization of the energy used to release a substance from a support can, at least in part, depend on the shape and dimensions of the support, the materials forming the support, and the placement of the support within the airway. In certain embodiments, the support can comprise an electrically resistive material such as a foil. In certain embodiments, the foil can be a stainless steel foil and can include a layer of one or more materials such as a gold layer to facilitate, for example, forming an electrical connection, and/or modifying the electrical properties such as the resistance of a portion of the foil. The appropriate dimensions for a foil can depend at least in part, on the desired resistance, the amount of substance disposed on the support, the amount of energy needed to vaporize the substance disposed on the support, and/or on mechanical stability considerations.

Figure 10:
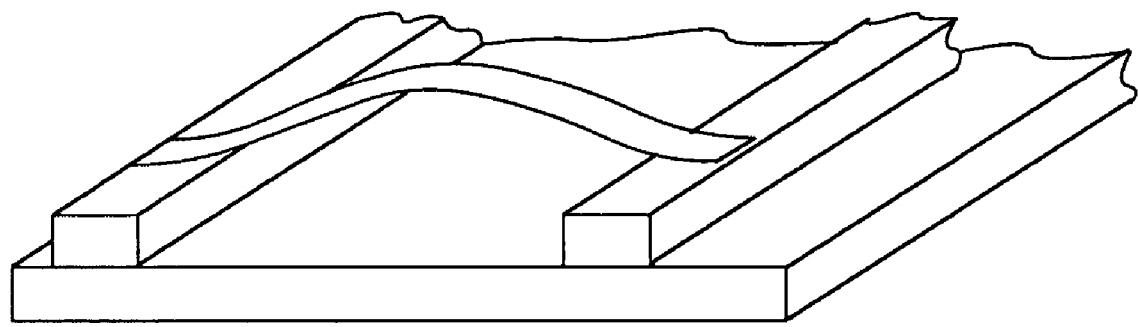
FIG. 10 is a schematic illustration showing a view of an arched metal foil according to certain embodiments.
Figure 11A:
FIG. 11 shows an example of the distortion of a flat metal foil, and an arched metal foil before and during resistive heating.
Figure 11B:
Figure 11C:
Figure 11D:
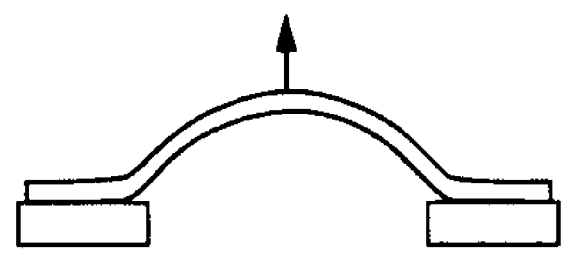

To maximize transfer of thermal energy produced by the support to the substance disposed thereon, it is desirable that a thermally conductive support be thermally isolated. Minimizing the contact area between the support and the connector helps to thermally isolate the support. As shown, for example, in FIG. 3, thermal isolation can be accomplished by suspending the support in the airflow above the surface of the structure by means of a spacer whereby the ends of the metal foil can be electrically connected to the power source. As shown in FIGS. 3, 8 and 10, in certain embodiments, the metal foil can be arched. During heating, thin foils can have a tendency to distort. This phenomenon is schematically illustrated in FIG. 11, where a metal foil is shown suspended between two conductors. FIG. 11(a) shows a flat metal foil spanning two conductors. During heating, the flat metal foil can distort as shown schematically in FIG. 11(b). In a multiple dose condensation aerosol delivery device comprising several metal foil supports, such mechanical distortion of the foils can interact with the airflow to increase deposition of the condensation aerosol particles on downstream surfaces. To facilitate the accuracy and reproducibility of the amount of substance released upon firing from each support or heating element and transferred to recipient, it can be desirable that the airflow characteristics of the device be consistent for each actuation of the device. While distortion of a metal foil can be minimized by using thicker foils, efficient heating of the metal foils with minimum power consumption indicates the use of thin foils. It has been found that the mechanical stability of a metal foil can be improved by producing a slight arch in the foil. An example of an arched foil is shown in FIG. 11(c). During heating, the arched metal foil shown in FIG. 11(c) can exhibit a slight upward movement as indicated in FIG. 11(d), and following heating returns to approximately the same arched configuration as prior to heating. The arch can be formed a number of ways, such as, for example, but not limitation, assembly by placing the metal foil, or plurality of metal foils over an arched mandrel and bonding the ends to a platform. The metal foil can be too thin to take a permanent set, but can be held in slight compression to maintain the arch. The platform on which the arched metal foil is mounted can be for example, a spacer such as spacer 80 as shown in FIG. 3, or can be structure 72 separating the first and second airways in embodiments where a spacer is not employed. In some embodiments of the invention, the height of the arch can ranges from 0.5 mm to 2 mm.

Particularly for portable, battery operated condensation aerosol delivery devices, it can be useful to minimize the amount of power used to vaporize a substance. Several characteristics of the metal foil can be chosen to facilitate the efficient thermal vaporization of a substance from a metal foil, including, but not limited to, the thickness of the metal foil, the impedance of the metal foil, and the ratio of the surface area to the thermal mass of the metal foil. In certain embodiments, the thickness of the metal foil can be less than 0.01 inches, in certain embodiments, less than 0.001 inches, and in certain embodiments, less than 0.0005 inches. To minimize power dissipation in the electrical circuit and thereby maximize power delivered to the heating element, it can be desirable that the impedance of the metal foil be closely matched to the impedance of the power source. For example, in certain embodiments, the difference between the impedance of the resistive heating element and the impedance of the power source can be less than 50% of the impedance of the power source, in certain embodiments, less than 10% of the impedance of the power source, and in certain embodiments, less than 2% of the impedance of the power source. To facilitate the efficient transfer of thermal energy produced by the resistive heating element to the substance disposed thereon, it can be useful to maximize the ratio of the surface area of the resistive heating element to the thermal mass of the resistive heating element. Accordingly, in certain embodiments the ratio of the surface area of the heating element to the thermal mass of the resistive heating element can be greater than 10 $cm^2/J/° C.$, in certain embodiments, greater than 100 $cm^2/J/° C.$, and in certain embodiments, greater than 500 $cm^2/J/° C.$ Low ratios of the surface area of the heating element to the thermal mass of the resistive heating element can facilitate the transfer of heat to the substrate, and lead to rapid thermal vaporization of the substance. Rapid thermal vaporization of a substance can minimize thermal degradation of the substance during vaporization and thereby maximize the purity of the condensation aerosol formed therefrom. For example, in certain embodiments, the support, and in particular, a metal foil can be heated to a temperature of at least 250° C. in less than 500 msec, in certain embodiments, to a temperature of at least 250° C. in less than 250 msec, and in certain embodiments, to a temperature of at least 250° C. in less than 100 msec.

Efficient transfer of thermal energy produced by the resistive heating element to the substance disposed thereon can further be facilitated by the substance being disposed on the surface as a thin layer. For example, in certain embodiments, the thickness of the layer of substance can range from 0.01 μm to 50 μm, in certain embodiments, can range from 0.01 μm to 20 μm, and in certain embodiments, can range from 0.01 μm to 10 μm.

The amount of energy to thermally vaporize a substance can be minimized by, for example, using an electrically resistive heating element comprising a thin metal foil, closely matching the impedance of the electrically resistive heating element to the impedance of the power source, maximizing the ratio of the surface area of the resistive heating element to the thermal mass of the resistive heating element, and using a thin film of substance disposed on the heating element. By appropriate design and selection of at least the foregoing parameters, in certain embodiments, the amount of energy to vaporize a substance from a support can be less than 250 joules, in certain embodiments, less than 50 joules, and in certain embodiments, less than 10 joules. In more specific embodiments, the amount of energy to vaporize one mg of substance from a support can be less than 250 joules, in certain embodiments, less than 50 joules, and in certain embodiments, less than 10 joules.

The number of supports forming a condensation aerosol delivery device and/or cartridge is not particularly limited. For example, in certain embodiments, a cartridge or drug delivery device can comprise from 1 to 200 supports, in certain embodiments, from 1 to 50 supports, and in certain embodiments, from 1 to 25 supports, and in certain embodiments, from 1 to 10 supports.

The cartridge can be separable from the condensation aerosol delivery device. In such embodiments, a subject can use the delivery device, for example, to administer more than one physiologically active substance, or more than one dose of the same physiologically active substance by replacing one cartridge with another. Also, when all the doses in a particular cartridge are exhausted, the user can obtain and insert a new cartridge into the delivery device.

While certain embodiments of the present disclosure can comprise a single support, it is contemplated that embodiments comprising a plurality of supports can be particularly useful in, for example, providing a convenient method of delivering multiple doses of a physiologically active compound or drug over a period of time. The terms physiologically active compound and drug are used interchangeably herein. As used herein, a drug refers to a substance recognized in an official pharmacopoeia or formulary, and/or a substance intended for use in the diagnosis, cure, mitigation, treatment or prevention of disease where disease refers to any disease, disorder, condition, symptom or indication. In such embodiments, the substance disposed on at least one support can comprise a therapeutically effective amount of a drug. For example, a therapeutically effective amount or dose of a drug can be disposed on a single support, on each of multiple supports, or on more than one support. In certain embodiments of a condensation aerosol delivery device, the same amount of physiologically active compound can be disposed on each support. In certain embodiments, different amounts of a physiologically active compound can be disposed on each of the plurality of supports, or a certain amount of active compound can be disposed on several supports, and a different amount of active compound on several other supports. Having different amounts of a drug on different supports can be useful in effecting treatment regimens where administering a variable amount of drug during a period of time is useful.

In certain embodiments, where the active compound disposed on several supports is an abusable substance, a second compound comprising an agonist can be disposed on one or more other supports. "Abusable substance" refers to a substance that can be improperly used, for example, by administering more than a prescribed or intended dosage, or by altering the route of administration from the intended route. For example, an opioid analgesic can be abused by using the opioid analgesic to elicit a euphoric effect, rather than therapeutically for the treatment of pain. Abusable substances include substances regulated by a regulatory agency focused on preventing drug abuse, such as, for example, the United States Drug Enforcement Agency (DEA). In certain embodiments, an abusable substance can be a substance listed on DEA schedule II, III, IV, or V. The second compound is a chemical compound that can act to reduce or to counteract the physiological activity and/or pharmacological effects of another chemical substance. Having both an abusable substance and a second compound capable of counteracting the effects of the abusable substance in the same device will complicate the ability of an abuser to selectively remove the abusable substance from heating elements. Proper use of the device would only allow the abusable substance to be activated in prescribed doses.

A substance to be released can be disposed on at least one surface of a support. For example, the substance can be disposed on the surface facing the center of the first airway and/or toward the part of the airflow where the velocity is highest. The substance can be applied to a surface of a support by any appropriate method and can depend at least in part on the physical properties of the substance and the final thickness of the layer to be applied. In certain embodiments, methods of applying a substance to a support include, but are not limited to, brushing, dip coating, spray coating, screen printing, roller coating, inkjet printing, vapor-phase deposition, spin coating, and the like. In certain embodiments, the substance can be prepared as a solution comprising at least one solvent and applied to a support. In certain embodiments, a solvent can comprise a volatile solvent such as acetone, or isopropanol. In certain embodiments, the substance can be applied to a support as a melt. In certain embodiments, a substance can be applied to a film having a release coating and transferred to a support. For substances that are liquid at room temperature, thickening agents can be admixed with the substance to produce a viscous composition comprising the substance that can be applied to a support by any appropriate method, including those described herein. In certain embodiments, a layer of substance can be formed during a single application or can be formed during repeated applications to increase the final thickness of the layer. In other embodiments, the substance can be applied on more than one surface of the support.

In certain embodiments, more than one active compound can be disposed on one or more of the plurality of supports. For example, a first active compound can be disposed on certain supports, and a second active compound can be disposed on other supports, and in certain embodiments, a composition comprising a first active compound and a second active compound can be disposed on one or more supports.

A dose can correspond to the amount of active compound released from a single support, or the amount of active compound released from more than one support. A dose or dosage as used herein refers to the amount of substance released during a single activation of a condensation aerosol delivery device. A dose can comprise a therapeutically amount of a physiologically active compound, meaning that the dose provides effective treatment of a condition and/or disease in a patient. The therapeutically effective amount of a physiologically active compound can vary from compound to compound, from subject to subject, and can depend upon factors such as the condition of the subject.

In certain embodiments, a substance disposed on at least one support can comprise a therapeutically effective amount of at least one physiologically active compound or drug. A therapeutically effective amount refers to an amount sufficient to effect treatment when administered to a patient or user in need of treatment. Treating or treatment of any disease, condition, or disorder refers to arresting or ameliorating a disease, condition or disorder, reducing the risk of acquiring a disease, condition or disorder, reducing the development of a disease, condition or disorder or at least one of the clinical symptoms of the disease, condition or disorder, or reducing the risk of developing a disease, condition or disorder or at least one of the clinical symptoms of a disease or disorder. Treating or treatment also refers to inhibiting the disease, condition or disorder, either physically, e.g. stabilization of a discernible symptom, physiologically, e.g., stabilization of a physical parameter, or both, and inhibiting at least one physical parameter that may not be discernible to the patient. Further, treating or treatment refers to delaying the onset of the disease, condition or disorder or at least symptoms thereof in a patient which may be exposed to or predisposed to a disease, condition or disorder even though that patient does not yet experience or display symptoms of the disease, condition or disorder. In certain embodiments, the amount of substance disposed on a support can be less than 100 micrograms, in certain embodiments, less than 250 micrograms, in certain embodiments, less than 500 micrograms, and in certain embodiments, less than 1,000 micrograms.

When delivering a pharmaceutical compound to a subject, the amount of substance that is vaporized off the surface is important. Consistency of delivery of the compound is also critical. In certain embodiments, at least 80% of the amount of material disposed on each support passes through the outlet of the device for deliver to the subject, in other embodiments, at least 90% passes through the outlet, and in other embodiments, at least 98% passes through the outlet.

In certain embodiments, a substance can comprise a pharmaceutical compound. In certain embodiments, the substance can comprise a therapeutic compound or a non-therapeutic compound. A non-therapeutic compound refers to a compound that can be used for recreational, experimental, or pre-clinical purposes. Classes of drugs that can be used include, but are not limited to, anesthetics, anticonvulsants, antidepressants, antidiabetic agents, antidotes, antiemetics, antihistamines, anti-infective agents, antineoplastics, antiparkinsonian drugs, antirheumatic agents, antipsychotics, anxiolytics, appetite stimulants and suppressants, blood modifiers, cardiovascular agents, central nervous system stimulants, drugs for Alzheimer's disease management, drugs for cystic fibrosis management, diagnostics, dietary supplements, drugs for erectile dysfunction, gastrointestinal agents, hormones, drugs for the treatment of alcoholism, drugs for the treatment of addiction, immunosuppressives, mast cell stabilizers, migraine preparations, motion sickness products, drugs for multiple sclerosis management, muscle relaxants, nonsteroidal anti-inflammatories, opioids, other analgesics and stimulants, ophthalmic preparations, osteoporosis preparations, prostaglandins, respiratory agents, sedatives and hypnotics, skin and mucous membrane agents, smoking cessation aids, Tourette's syndrome agents, urinary tract agents, and vertigo agents.

Examples of pharmaceutical compounds include fluticasone propionate, clonidine, triazolam, albuterol, ciclesonide, fentanyl, terbutaline, flumazenil, triamcinolone acetonide, flunisolide, ropinirole, alprazolam, buprenorphine, hyoscyamine, atropine, pramipexole, bumetanide, flunitrazepam, oxymorphone, colchicine, apomorphine HCl, granisetron, pergolide, nicotine, loperamide, azatadine, naratriptan, clemastine, benztropine, ibutilide, butorphanol, fluphenazine, estradiol-17-heptanoate, zolmitriptan, metaproterenol, scopolamine, diazepam, tolterodine, estazolam, haloperidol, carbinoxamine, estradiol, hydromorphone, bromazepam, perphenazine, midazolam, methadone, frovatriptan, eletriptan, testosterone, melatonin, galanthamine, cyproheptadine, bropheniramine, and chlorpheniramine. In certain embodiments, the compound is chosen from alprazolam, buprenorphine, clonindine, fentanyl, midazolam, pramipexole, ropinirole, and triazolam. In certain embodiments, the compound is chosen from a compound for the treatment of pain. In certain embodiments, the compound for the treatment of pain is fentanyl.

In certain embodiments, a drug can further comprise substances to enhance, modulate and/or control release, aerosol formation, intrapulmonary delivery, therapeutic efficacy, therapeutic potency, stability, and the like. For example, to enhance therapeutic efficacy a drug can be co-administered with one or more active agents to increase the absorption and/or diffusion of the first drug through the pulmonary alveoli, or to inhibit degradation of the drug in the systemic circulation. In certain embodiments, a drug can be co-administered with active agents having pharmacological effects that enhance the therapeutic efficacy of the drug. In certain embodiments, a drug can comprise compounds that can be used in the treatment of one or more diseases, conditions, or disorders. In certain embodiments, a drug can comprise more than one compound for treating one disease, condition, or disorder, or for treating more than one disease, condition, or disorder.

In certain embodiments, the substance can comprise one or more pharmaceutically acceptable carriers, adjuvants, and/or excipients. Pharmaceutically acceptable refers to approved or approvable by a regulatory agency of the Federal or a state government or listed in the U.S Pharmacopoeia or other generally recognized pharmacopoeia for use in animals, and more particularly in humans.

In general, substances useful in embodiments of the disclosure can exhibit a heat of vaporization less than about 150 kJoules/mol.

Not only can the amount of compound forming a dose be impacted by deposition of aerosol particles on the device and other supports in the device, but the amount of compound forming a dose can be reduced by degradation of the active agent during release from the support. While it will be recognized that the extent and dynamics of thermal degradation can at least in part depend on a particular compound, in certain embodiments, thermal degradation can be minimized by rapidly heating the substance to a temperature sufficient to vaporize and/or sublime the active substance. In certain embodiments, the support or heating element can be heated to a temperature of at least 250° C. in less than 500 msec, in certain embodiments, to a temperature of at least 250° C. in less than 250 msec, and in certain embodiments, to a temperature of at least 250° C. in less than 100 msec.

In certain embodiments, rapid vaporization of a layer of substance can occur with minimal thermal decomposition of the substance, to produce a condensation aerosol exhibiting high purity of the substance. For example, in certain embodiments, less than 10% of the substance is decomposed during thermal vaporization resulting in a condensation aerosol with at least 90% purity and in certain embodiments, less than 5% of the substance is decomposed during thermal vaporization resulting in a condensation aerosol with at least 95% purity, and in other embodiments, less than 2% of the substance is decomposed during thermal vaporization resulting in a condensation aerosol with at least 98% purity.

For administration of a compound, the size of the particulates of the compound comprising the aerosol can be within a range appropriate for intrapulmonary delivery. Without being limited by theory, an aerosol having a mass median aerodynamic diameter ("MMAD") ranging from 1 µm to 3 µm, and ranging from 0.01 µm to 0.10 µm are recognized as optimal for intrapulmonary delivery of pharmaceutical compounds. Aerosols characterized by a MMAD ranging from 1 µm to 3 µm can deposit on alveoli walls through gravitational settling and can be absorbed into the systemic circulation, while aerosols characterized by a MMAD ranging from about 0.01 µm to 0.10 µm can also be deposited on the alveoli walls through diffusion. Aerosols characterized by a MMAD ranging from 0.15 µm to 1 µm are generally exhaled. Thus, in certain embodiments, aerosols produced using devices and methods of producing an aerosol can having a MMAD ranging from 0.01 µm to 5 µm, in certain embodiments, a MMAD ranging from 0.05 µm to 3 µm, in certain embodiments, a MMAD ranging from 1 µm to 3 µm and in certain embodiments, a MMAD ranging from 0.01 µm to 0.1 µm. In certain embodiments, aerosols suitable for intrapulmonary delivery of pharmaceutical compounds can further be characterized by the geometric standard deviation of the log-normal particle size distribution. In certain embodiments, aerosols produced using the devices and methods of producing an aerosol comprise a geometric standard deviation of the log-normal particle size distribution of less than 3, in certain embodiments, less than 2.5, and in certain embodiments, less than 2.

Figure 12:
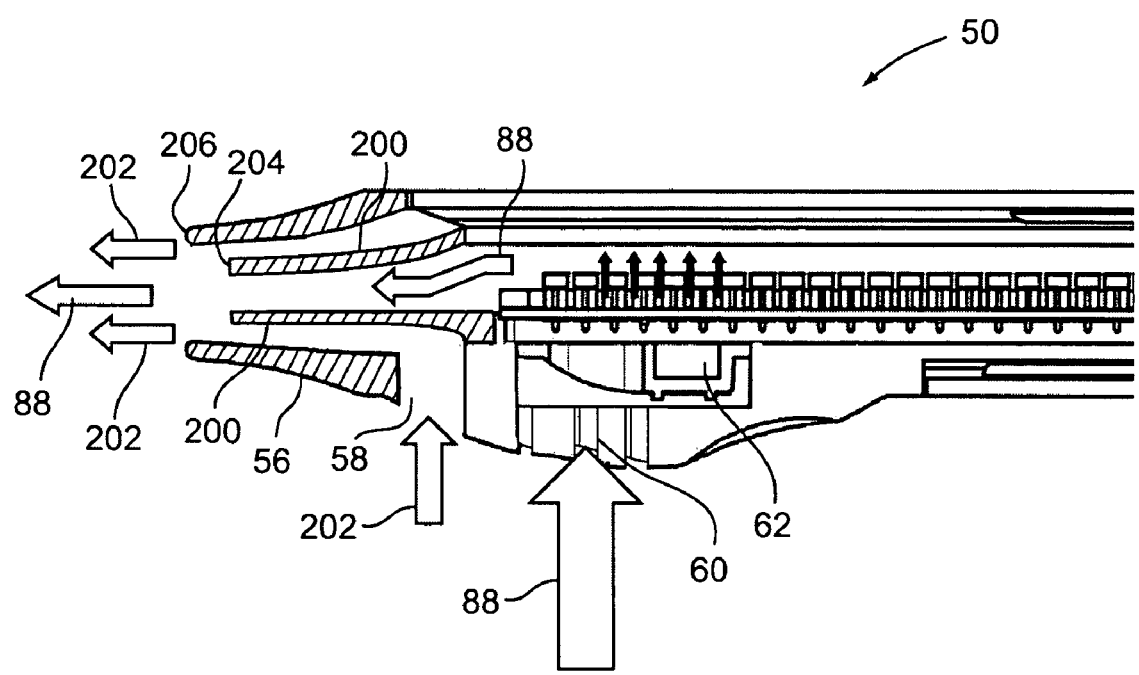
FIG. 12 is a partial cross-sectional view of a separable cartridge including air routing according to certain embodiments.

In certain embodiments, a cartridge can include a part disposed in the mouthpiece to control the airflow exiting the device. A partial section view of the cartridge cross-section of FIG. 5 is shown in FIG. 12. FIG. 12 shows the front section of cartridge 50, further including an air routing part 200 disposed within the mouthpiece 56. The airflow 88 entering air intake 60, and air inlet valve 62 passes through the internal airways to entrain a condensation aerosol particles, and passes through the orifice defined by air routing part 200 to be emitted from the device. Bypass airflow 202 enters bypass opening 58 and is diverted around the outside of air routing part 200. The front 204 of air routing part 200 extends to near the tip 206 of mouthpiece 56. The use of air routing part 200 can be useful in maintaining smooth airflow through the device and facilitating control of the condensation aerosol particle size.

An embodiment of a condensation aerosol delivery device is the portable electric multi-dose drug delivery systems discussed herein, and illustrated in FIGS. 7 to 9. The electric multi-dose drug delivery system is designed to produce and deliver a therapeutic condensation aerosol into the respiratory tract, and in particular to the pulmonary pathway, of a subject. As discussed herein, the condensation aerosol delivery device includes two subsystems, referred to as the cartridge and the dispensing unit. Both the cartridge and the dispensing unit incorporate several electronic features which facilitate the portability, safety, versatility, and convenience of the delivery device. As disclosed herein, the cartridge includes the therapeutic drug in individual doses, and electronics to sense airflow generated by the subject's inhalation. The dispensing unit includes a battery power source, and a microcontroller that controls the drug vaporization process, and can include a number of communication functions. Such communication functions include, but are not limited to, cartridge identification, dose identification, abuse prevention functions, use monitoring, and dose control.

Figure 13:
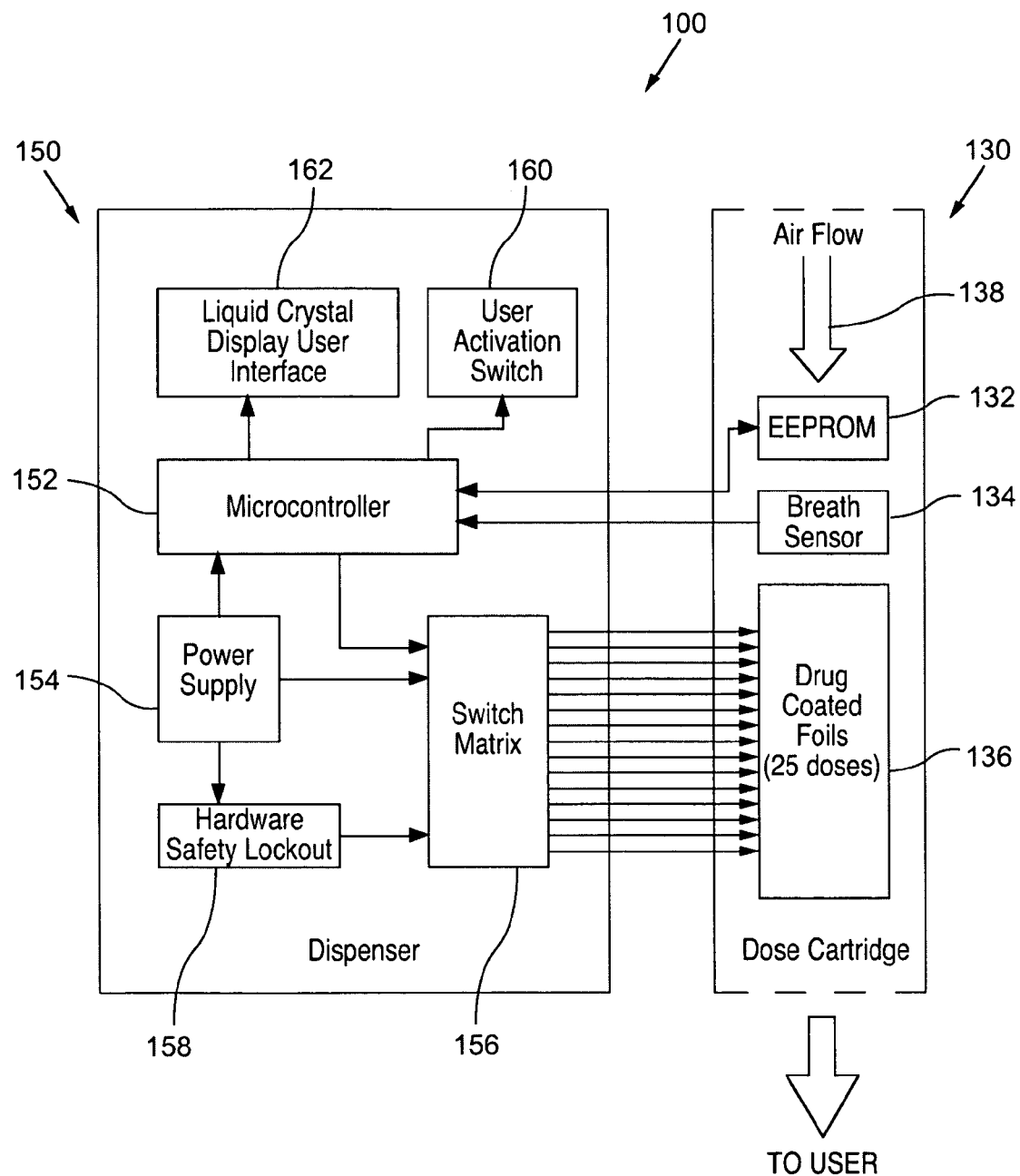
FIG. 13 is a block diagram of an embodiment the electrical functions for an electric multi-dose condensation aerosol delivery device.

A functional block diagram of the electronics for an exemplary embodiment of an electric multi-dose condensation aerosol delivery device 100 is shown in FIG. 13. FIG. 13 shows a cartridge 130 comprising an EEPROM 132, a breath sensor 134, and twenty-five drug coated metal foils 136. EEPROM 132 can include, for example, an identifying serial number for the cartridge, a manufacturing date, and/or additional identification and control information, and monitors the number of doses remaining in the cartridge. EEPROM 132 is electrically connected to microcontroller 152 contained in the dispensing unit 150. Microcontroller 152 can read or write to EEPROM 132 to update and record the data stored therein. EEPROM 132 need not require power to maintain the data. Breath actuation sensor 134 includes circuitry for detection of airflow, and is electrically connected to microcontroller 152. The circuitry can comprise two temperature sensing devices such as thermistors, one of which is heated. Air flowing across the heated sensor 134 is transduced as a change in voltage, which is monitored by microcontroller 152. When a certain minimum velocity of airflow 138 is sensed, microcontroller 152 connects power source 154 to at least one of resistive metal foils 136 to effect vaporization of the drug disposed thereon. Plurality of drug coated foils 136 are electrically connected to a switch matrix 156 which is controlled by microcontroller 152. As disclosed herein, plurality of drug coated foils 136 can be selectively heated by passing a current through the foils to vaporize the drug coating to form a condensation aerosol in airflow 138.

As shown in FIG. 13, dispensing unit 150 includes microcontroller 152, power source 154, switch matrix 156, a hardware safety lock-out mechanism 158, a user-activated switch 160, and a liquid crystal display user interface 162. Microcontroller 152 incorporates embedded software and controls operation of the condensation aerosol delivery device. When not operating, microcontroller 152 is maintained in a sleep mode to conserve power consumption. Upon momentary depression of user activation switch 160, microcontroller 152 becomes operational. In certain embodiments, microcontroller 152 can also be activated by inserting a cartridge into the delivery device. Microcontroller 152 can then check for the presence of cartridge 130, and if present, microcontroller 152 reads EEPROM 132 to determine whether the serial number of cartridge 130 matches the serial number stored in the controller, and calculates the number of unused doses contained on drug coated foils 136 remaining in cartridge 130. A purpose of matching the cartridge and dispensing unit serial number can be to personalize individual cartridges 130 and dispensing unit 150 to an individual patient. Personalization can be programmed using the embedded software by a health care provider to facilitate and personalize a patient's treatment regimen, and to reduce the potential for abuse by preventing a particular cartridge from being used in a dispensing unit having a different serial number. Upon verification of the parameters, microcontroller 152 updates display 162 with, for example, the number of doses remaining in cartridge 130, and waits for an activation signal from breath sensor 134. When a patient establishes a sufficient airflow in cartridge 130 by inhaling on the cartridge mouthpiece, microcontroller 152 connects power source 154, through switch matrix 156, to one or more of drug coated foils 136 to release the drug to form a condensation aerosol comprising the drug in airflow 138 of cartridge 130 that is inhaled by the patient. Microcontroller 152 is electrically connected to switch matrix 156, and can connect one or more of drug-coated foils 136 to power source 154 at a given time. In certain embodiments, microcontroller 152 can connect one or more drug coated foils 136 to power source 154 sequentially, randomly, or in a predetermined order. Following actuation to deliver a dose to the patient, microcontroller 152 can enter a lockout period in which a subsequent dose cannot be released until the lockout period expires. Microcontroller 152 can enter a sleep mode to conserve power until manually activated by depressing user activation switch 160, inserting a cartridge in the device, and/or removing a cartridge.

Display 162 is an electronic display which can inform a user of the current state of the device, e.g., whether the device is in the sleep or activated mode, and the number of unused doses remaining in the cartridge. User activated switch 160 is a momentary push button switch that when depressed activates the system from the sleep mode. Power source 154 comprises three alkaline primary cells that are used to power the system including providing the power necessary to vaporize the drug disposed on metal foils 136. Switch matrix 156 can be an array of MOSFET switches under control of the microcontroller that couple power from power source 154 to the appropriate drug coated foils 136. Hardware safety lockout 158 is a redundant, software-independent system that can prevent more than one dose from being delivered at a time and/or prevent a second dose from being delivered before the end of the lockout period. Hardware safety lockout 158 provides a redundant safety mechanism in the event of software malfunction.

In certain embodiments, the device is such that the total airflow passing through the outlet ranges from 10 liters/min to 100 liters/min. In other embodiments, the total airflow passing though the outlet ranges from 20 liters/min to 90 liters/min.

In certain embodiments of the device, the airflow rate through the inlet is less than 100 L/min. In other embodiments, the airflow rate through the inlet is less than 50 liters/min. In yet other embodiments, the airflow rate through the inlet is less than 25 liters/min; and in still other embodiments, the airflow rate through the inlet is less than 10 liters/min.

It should also be evident from the various embodiments disclosed herein that many parameters can be selected and/or adjusted to provide a condensation aerosol delivery device, and in particular an electric condensation aerosol delivery device capable of delivering multiple doses of a physiologically active substance to a patient with each dose being delivered during a single inhalation. It will be appreciated that at least some of the parameters are interactive, and that the multiple parameters can be adjusted by routine optimization procedures to generate a condensation aerosol comprising a dose of a particular physiologically active substance. As discussed herein, such parameters include, but are not limited to the properties of a particular substance, e.g., heat of vaporization, the quantity of substance comprising a dose, the thickness of the layer disposed on the support, the thickness of the heating element, the ratio of the surface area of the heating element to the thermal mass of the resistive heating element, and the airflow.

EXAMPLES

Embodiments of the present disclosure can be further defined by reference to the following examples, which describe in detail certain embodiments of the present disclosure. It will be apparent to those skilled in the art that many modifications, both to materials and methods, may be practiced without departing from the scope of the present disclosure.

Example 1

Electric Multi-Dose Condensation Aerosol Delivery Device

Electric multiple dose condensation aerosol delivery devices as shown in FIGS. 2-5 were fabricated. The two halves forming the housing of the cartridge were molded from either acrylonitrile-butadiene-styrene or polycarbonate. The structure separating the first and second airways was fabricated from 0.032-inch thick FR4 printed circuit board material. When assembled, the circuit board and the walls of the cartridge define a 3.5 inch long first airway having a cross-sectional area of 1.5 $cm^2$, and a 3.0 inch long second airway having a cross-sectional area of 1.5 $cm^2$. The total resistance through the cartridge was 0.07 sqrt(cm-$H_2O$)/L/min at a total airflow rate of 20 L/min and 0.09 sqrt(cm-$H_2O$)/L/min at 90 L/min. The flow valve was designed to control the flow between 4 L/min and 8 L/min for a total flow rate ranging from 20 L/min to 90 L/min (see FIG. 4). Circuit boards used to separate the first and second airways were fabricated having different arrangements and dimensions of holes. In a certain exemplary embodiment, the plurality of holes beneath the metal foils comprised an array of 100 round holes situated beneath the gaps between adjacent metal foils. Sixty percent of the airflow entering the air control valve passed through a series of slots and across the heating elements in the first airway. Forty percent of the airflow passed through the plurality of holes in the circuit board and was directed toward the heating elements and the center of the first airway.

The device incorporated 25 supports. The supports were fabricated from 0.0005 inch thick stainless steel foils having a surface area of 0.2 $cm^2$ and mounted in an arched configuration to minimize distortion during heating. Fifty μg of fentanyl was deposited on the surface of each foil by spray coating from a solution comprising either isopropyl alcohol, acetone, or acetonitrile. The 50 μg layer of fentanyl was 3 μm thick. The resistance of the metal foils on which the fentanyl was deposited was 0.4 Ω, the ratio of the surface area of the metal foil to the thermal mass of the heating foil was 47 cm²/J/C. Either three AAA batteries or a Hewlett Packard 6002A DC power supply were used, depending on the experiment conducted, to provided 1.7 joules of energy to the heating element to vaporize the 50 μg of fentanyl.

Example 2

Aerosol Particle Size Measurement

The size of aerosol particles can impact the therapeutic efficacy of a pharmaceutical administered by inhalation. For example, aerosols having a particle size ranging from 0.01 μm to 3 μm are considered optimal for pulmonary delivery. In addition to the dynamics of aerosols during inhalation, it can be important that a condensation aerosol delivery device generate a consistent and reproducible particle size distribution. Aerosol particle size can be characterized by the mass median aerodynamic diameter (MMAD) of the aerosol. MMAD refers to the median of the distribution of particle sizes forming the aerosol.

Figure 14:
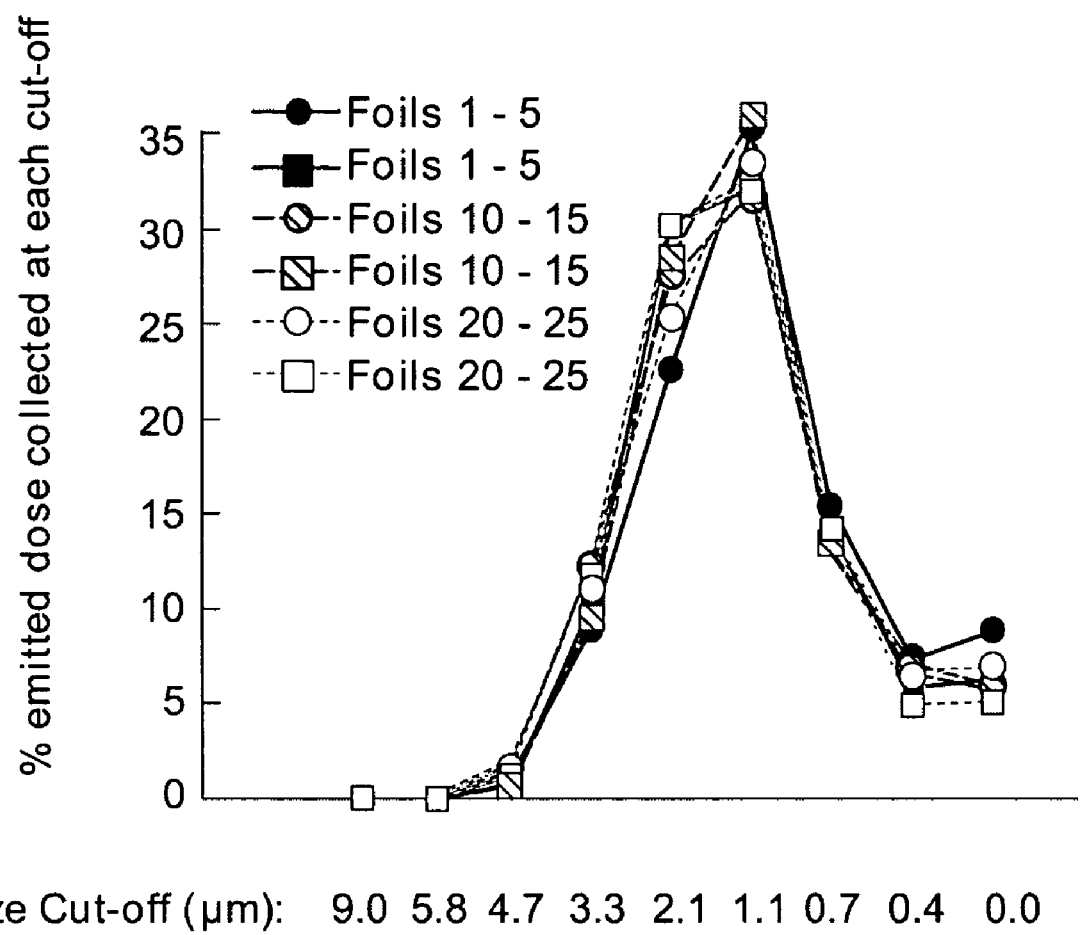
FIG. 14 shows the particle size distribution of a condensation aerosol comprising a substance emitted from an electric multi-dose condensation aerosol delivery device according to certain embodiments.

Aerosol particle size distributions for condensation aerosols formed using the condensation aerosol delivery device described in Example 1 are presented in FIG. 14. Each foil of a 25-foil cartridge contained 50 μg of fentanyl as a 3 μm thick layer. A single foil was heated to a peak temperature of 400° C. within 350 msec in a 6 L/min airflow. The particle size distribution of the aerosol emitted from the device was measured by the Anderson Impaction method using an eight stage Cascade Impactor Series 20-800 Mark II (Anderson, Copley Scientific, Nottingham, UK). The particle size distribution for two replicates from each of front foils (1-5), middle foils (10-15) and back foils (20-25) (closest to the mouthpiece) are presented in FIG. 14. The particle size distribution of the aerosol from each foil is consistent, exhibiting a range of particle size from about 5.8 μm to about 0 μm with a MMAD of 1.8 μm, and a geometric standard deviation (GSD) of 1.7 μm.

Example 3

Effect of Airflow on Particle Size

The airflow in a condensation aerosol delivery device as described in Example 1 was adjusted and the particle size of five emitted doses measured using the Anderson impaction method. The airflow volume was increased from 4 L/min to 8 L/min to increasing the airflow velocity from 1 m/sec to 2 m/sec. In tests 1, 2, and 4, a bypass air routing part was inserted into the mouthpiece section of the cartridge (to get the total airflow up to 28.3 L/min for the Andersen impactor to function properly) such that the bypass air and the airflow containing the condensation aerosol joined just prior to entering the impactor. In test 3, however, bypass air was introduced into the outgoing airflow immediately after passing over the heating elements. The results are presented in Table 1.

TABLE 1

Effect of Airflow Rate on Aerosol Particle Size

|  | Test 1 | Test 2 | Test 3 | Test 4 |
| --- | --- | --- | --- | --- |
| Airflow Rate (L/min) | 4 | 6 | 6 | 8 |
| Airflow Velocity (m/sec) | 1 | 1.5 | 1.5 | 2 |
| Percent Recovery | 83 | 90 | 86 | 90 |
| Emitted Dose (μg) | 208 | 225 | 216 | 224 |

TABLE 1-continued

Effect of Airflow Rate on Aerosol Particle Size

|  | Test 1 | Test 2 | Test 3 | Test 4 |
| --- | --- | --- | --- | --- |
| MMAD (μm) | 2.53 | 1.88 | 1.37 | 1.25 |
| GSD | 1.99 | 2.09 | 2.36 | 2.10 |
| FPF (1-3.5 μm) (%) | 56 | 61 | 60 | 58 |
| Fraction 0-2 μm (%) | 37 | 53 | 69 | 76 |
| Fraction <5 μm (%) | 91 | 98 | 100 | 100 |

Example 4

Stability of Fentanyl in Multi-Dose Device

Figure 15:
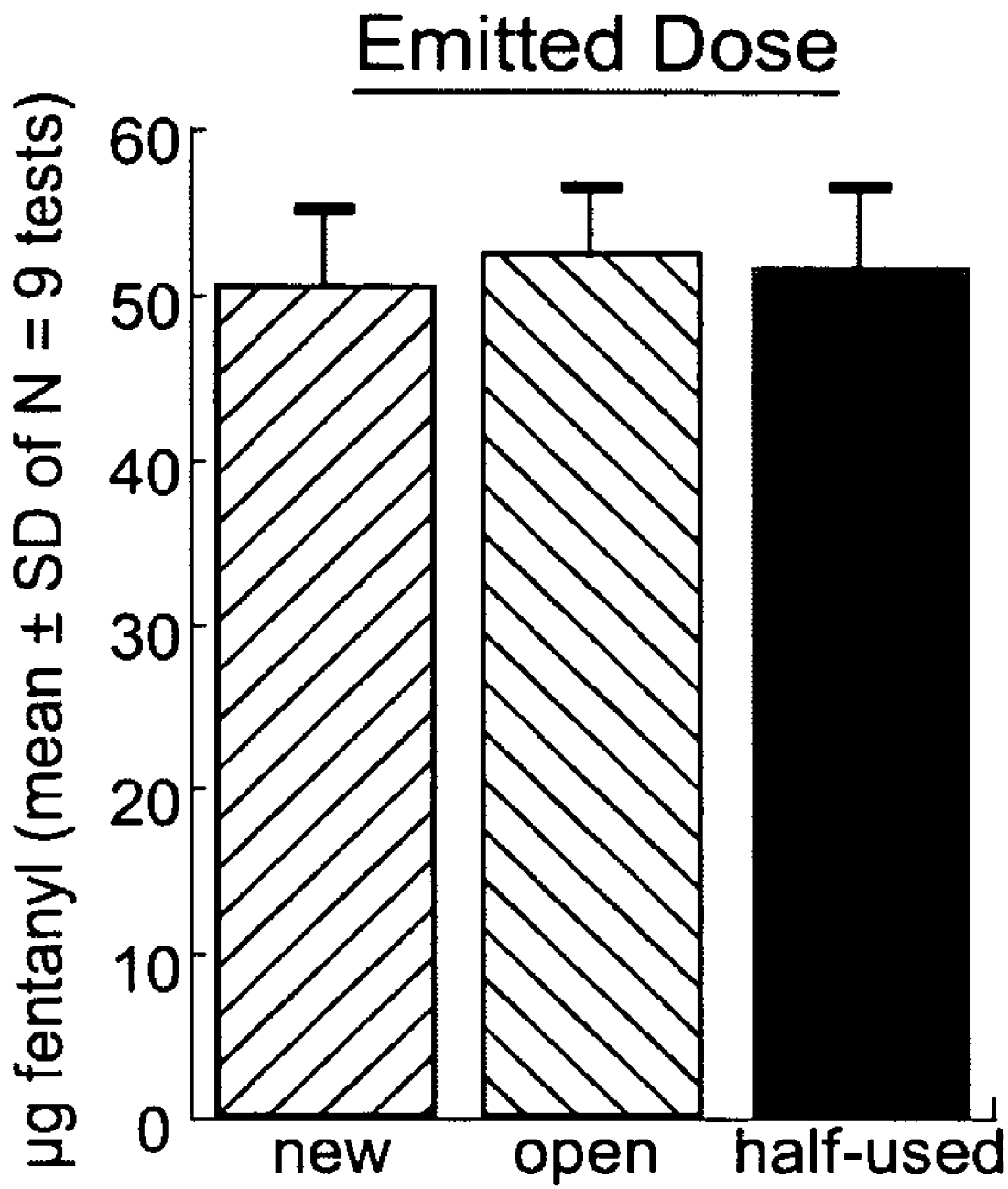
FIG. 15 shows the reproducibility of the amount and purity of doses of fentanyl emitted from a new, an opened, and a partially-used electric multi-dose condensation aerosol delivery device according to certain embodiments.

The stability of fentanyl in multi-dose condensation aerosol delivery devices was determined by measuring the amount and purity of fentanyl in an emitted dose for a newly manufactured cartridge (diagonal lines), an unused cartridge that was stored at room temperature for 7 days (cross-hatch), and a cartridge that was used to emit 10 doses and then stored at room temperature for 7 days (solid). The results are presented in FIG. 15.

Example 5

Temperature Profile of Heating Element

Figure 16:
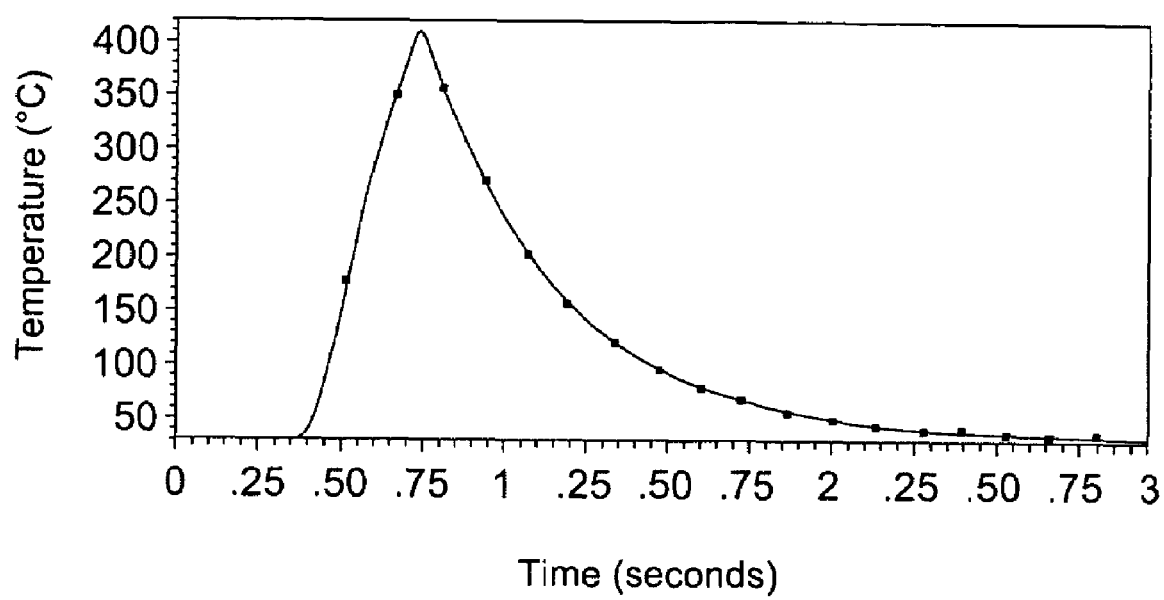
FIG. 16 shows a temperature profile of a metal foil in an airflow according to certain embodiments.

Three AAA batteries provided 1.7 joules of energy to a 0.0005 inch thick stainless steel foil on which 50 μg of fentanyl was deposited. The airflow velocity was 1 m/sec corresponding to an airflow rate of 4 L/min. As shown in FIG. 16, the temperature of the foil increased to a temperature of about 200° C. within 50 msec, a maximum temperature of 400° C. within 284 msec, and returned to room temperature within 1.5 sec after reaching maximum temperature.

Example 6

Temperature Uniformity Measurements

Figure 17A:
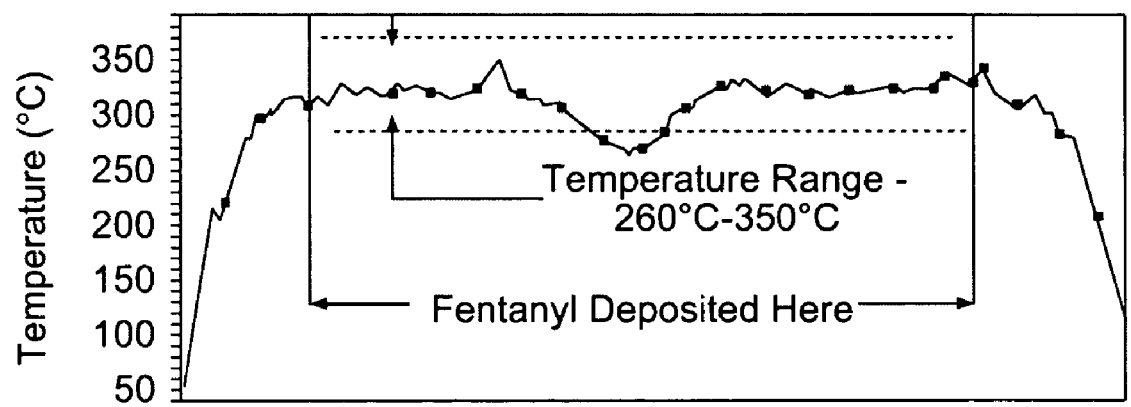
FIGS. 17A and 17B show the temperature uniformity of a metal foil in an airflow with fentanyl as the substance according to certain embodiments.
Figure 17B:
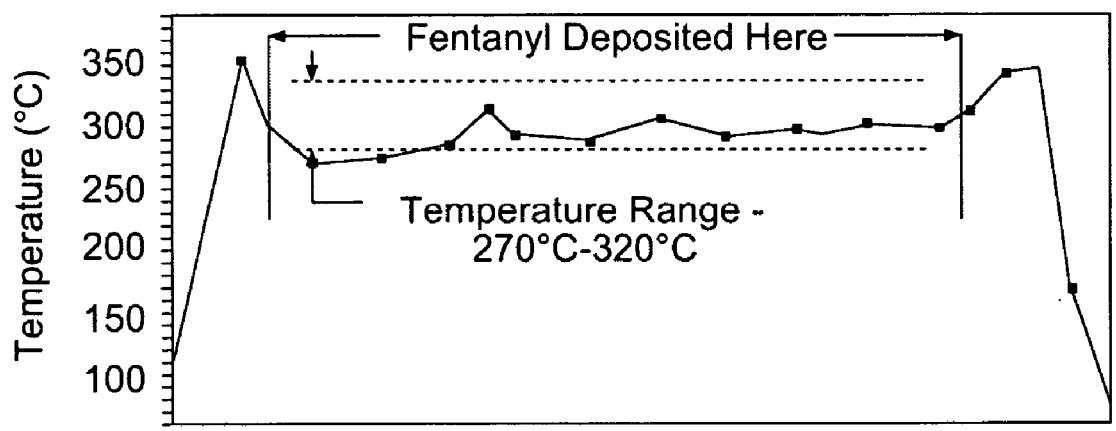

The temperature uniformity of a foil having a thin layer of 50 μg of fentanyl was measured during heating. The results are shown in FIGS. 17A and 17B.

Example 8

Effect of Second Airflow on Aerosol Particle Deposition

Figure 18:
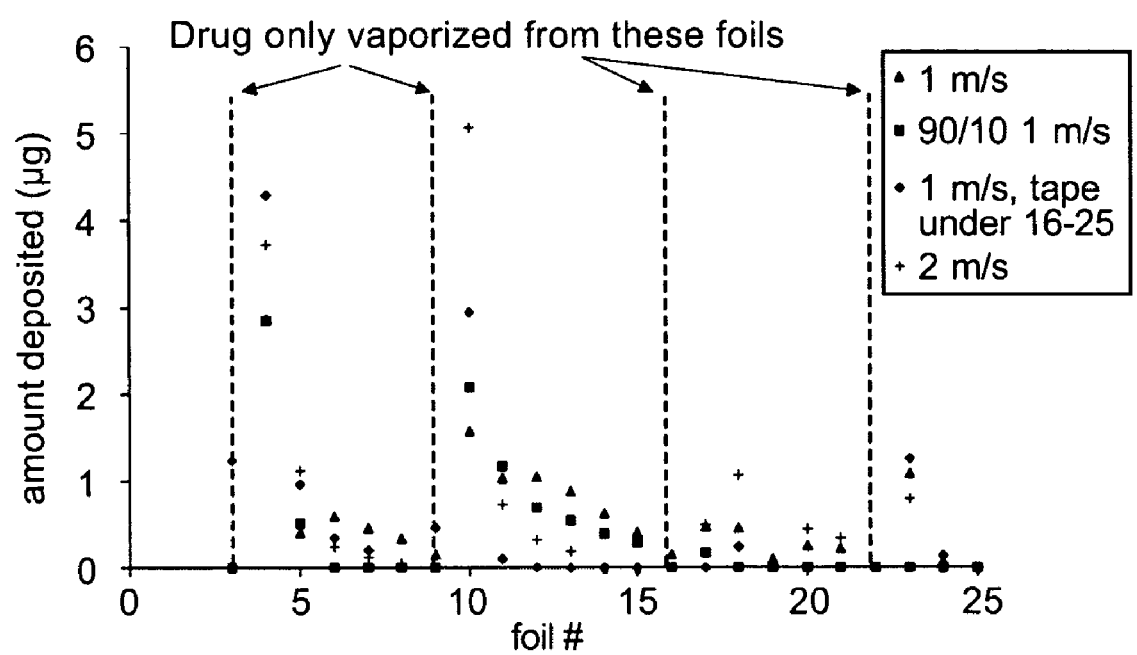
FIG. 18 shows the amount of substance deposited on downstream heating elements from vaporized substances from preceding heating elements for different airflow velocities with little or no airflow directed upward from underneath the heating elements.
Figure 19:
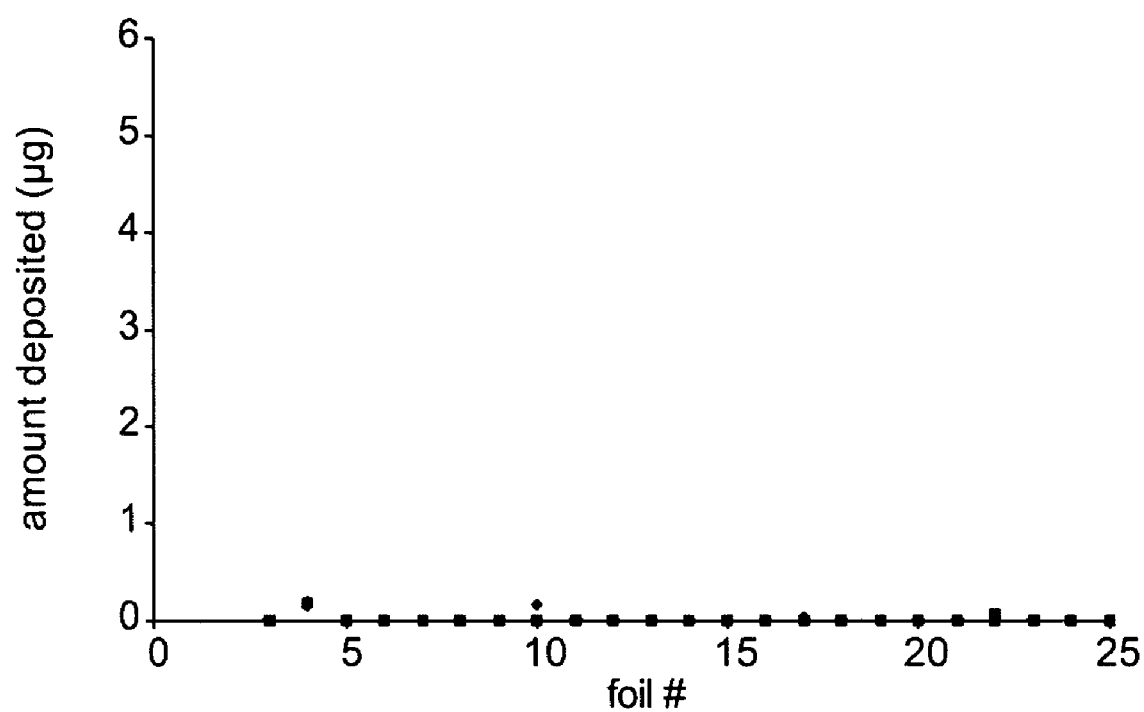
FIG. 19 shows the amount of substance deposited on downstream heating elements from vaporized doses with a percentage of the total airflow directed upward from underneath the heating elements, where the airflow distribution was controlled by a layer of foam between the first and second airways.

The effects of the airflow in a cartridge on the deposition of the aerosol particles on downstream surfaces is demonstrated in FIGS. 18 and 19. The results presented in FIG. 18 were obtained using a cartridge as described in Example 1 with the exception that there was no circuit board separating the first and second airways and flow was controlled by flow meters instead of a flow valve. The heating elements were supported at the edges only and there was no flow control between the first and second airways; the amount of air entering the first and second airways was controlled by flow meters at the inlet to each airway. For the 1 m/s and 2 m/s examples in FIG. 18 the first and second airways were separated by a piece of tape to test aerosol particle deposition when all the airflow passed over the top of the heating elements. In the 90/10 1 m/s example, in contrast, the tape was removed and the flow meters were set such that 90% of the inlet airflow entered through the first airway and 10% entered through the second airway. The air that entered through the second airway had to flow through the gaps between the heating elements to reach the airway outlet. Finally, in the 1 m/s, tape under 16-25 case a piece of tape was placed below heating elements 16-25 and again the flow meters were set such that 90% of the inlet airflow entered through the first airway and 10% entered through the second airway. The tape was intended to increase the amount of air flowing up past heating elements 1-15. In each experiment heating elements 3, 9, 16, and 22 contained a 3 µm thick layer of 50 µg of fentanyl from which fentanyl was vaporized, with the downstream elements fired before the upstream elements so that any deposited aerosol particles would not be revaporized. As shown in FIG. 18, for each of these conditions up to about 5 µg of fentanyl was deposited on each downstream heating element.

FIG. 19 shows the results from three tests conducted using the same airway as described above for the results in FIG. 18. In these tests, however, the first and second airways were separated by a thin piece of foam placed directly below the heating elements and the flow meters were set such that 50% of the inlet airflow entered through the first airway and 50% entered through the second airway. The foam created a pressure drop between the first and second airway, evenly distributing the flow from the second airway past each heating element and into the center of the first airway. In these experiments 50 µg of fentanyl were vaporized from each of the 25 heating elements (in contrast to the experiments from FIG. 18 where fentanyl was only vaporized from 4 heating elements) from downstream heating element 25 to upstream heating element 1, and essentially no fentanyl was deposited on the downstream heating elements.

Example 9

Purity and Yield of Emitted Dose

Figure 20A:
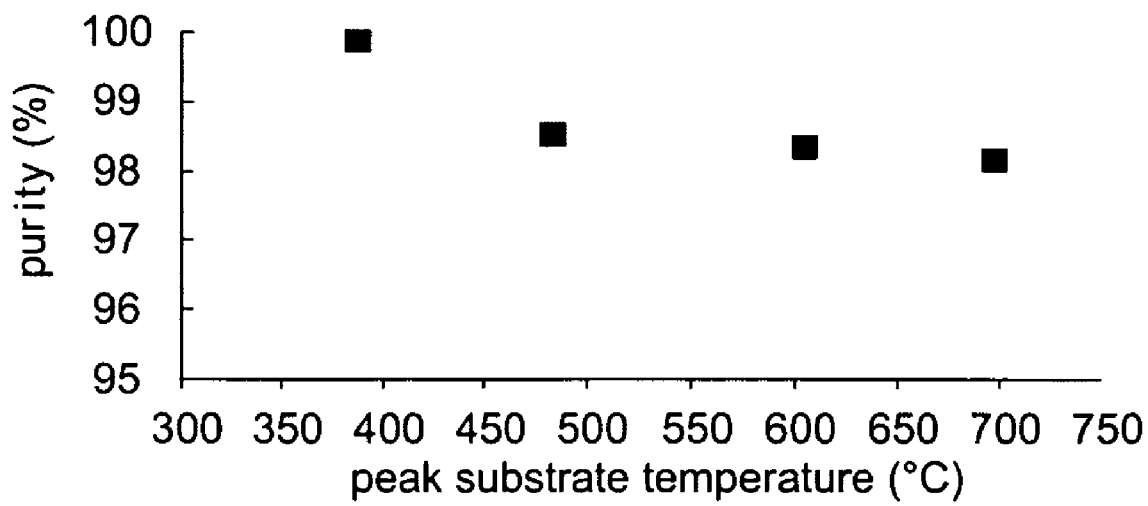
FIGS. 20A and 20B show a relationship between the temperature of a metal foil and the purity and amount of the dose emitted from an electric multi-dose condensation aerosol delivery device according to certain embodiments.
Figure 20B:
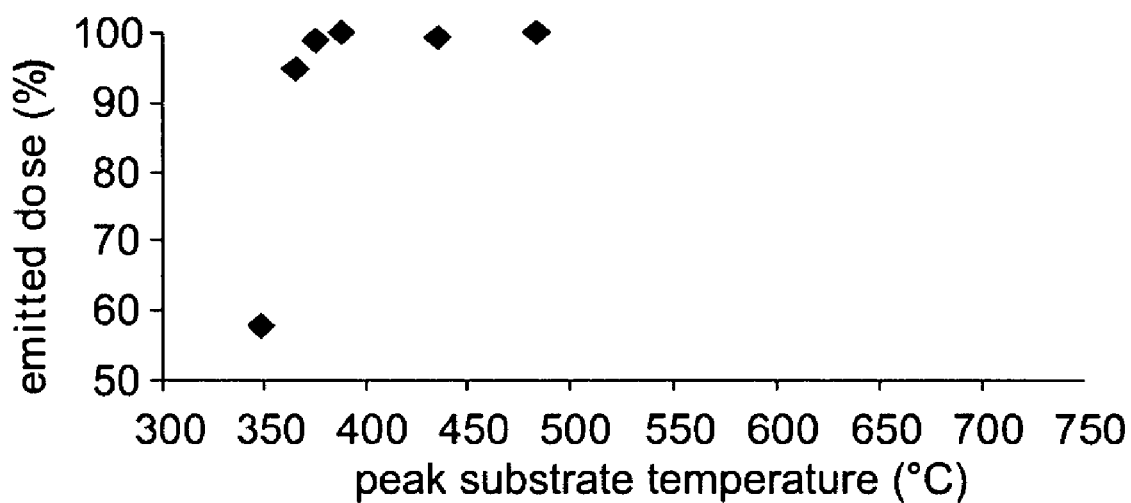

The purity and yield of emitted doses for devices as described in Example 1, except that the surface area of each support was 0.25 cm$^2$, are presented in FIGS. 20A and 20B. FIG. 20A shows that the purity of a 2.4 µm thick, 60 µg dose of fentanyl emitted from the device is greater than 98% when the peak temperature of the heating element is at least 375° C. As shown in FIG. 20B, at least 96% of the 2.4 µm thick, 60 µg dose of fentanyl disposed on a heating element was emitted from the device when heated to a temperature of at least 375° C. For FIGS. 20A and 20B, the condensation aerosols comprising fentanyl were characterized by a MMAD of 2.0 µm and a GSD of 1.8 µm.

What is claimed is:

1. A device for entraining a substance within an airflow comprising:
    an airway comprising an inlet, and an outlet;
    a plurality of supports disposed within the airway;
    a substance disposed on at least one of the plurality supports;
    a mechanism configured to release the substance from each of the at least one of the plurality of supports; and
    airflow routing means for routing an airflow within the airway to entrain the substance in the airflow when released from a support and for inhibiting deposits of the substance on any other support.

2. A device for producing a condensation aerosol in an airflow comprising:
    an airway comprising an inlet, and an outlet;
    a plurality of supports disposed within the airway;
    a substance disposed on at least one support of the plurality of supports;
    a mechanism configured to vaporize the substance from each support of the plurality of supports on which the substance is disposed; and
    airflow routing means routing an airflow within the airway to forms condensation aerosol particles from the vaporized substance that is entrained in the airflow when vaporized and for inhibiting deposits of aerosol particles on any other support.

3. The device of claim 2, wherein each support of the plurality of supports comprises an electrically resistive heating element.

4. The device of claim 2, wherein is the airflow routing means comprises a first airflow between the inlet and the outlet and a second airflow directed through a plurality of holes toward the supports and the first airflow, wherein as the substance forms condensation aerosol particles the particles are entrained in the first airflow and directed away from the plurality of supports by the second airflow.

5. The device of claim 3, wherein each support comprises a metal foil.

6. A device for delivering a condensation aerosol comprising a substance to a subject comprising:
    a housing;
    an airway contained within the housing comprising an inlet, and an outlet;
    a mouthpiece coupled to the outlet;
    at least one support disposed within the airway;
    the substance disposed on the at least one support;
    a mechanism configured to vaporize the substance;
    a power source for powering the mechanism configured to vaporize the substance;
    an actuation mechanism configured to transfer energy from the power source to the mechanism configured to vaporize the substance; and
    airflow routing means for routing an airflow within the airway to form a condensation aerosol from the vaporized substance and to substantially prevent the condensation aerosol from being deposited within the airway.

7. The device of claim 6, further comprising an air bypass hole coupled to the outlet.

8. A device for delivering a condensation aerosol comprising a substance to a subject comprising:
    a dispensing unit comprising:
        a first housing comprising a receptacle for a separable cartridge;
        a controller for controlling vaporization of the substance; and
        a power source; and
    a separable cartridge comprising:
        a second housing;
        an airway contained within the housing having an inlet, and an outlet;
        a mouthpiece coupled to the outlet;
        a plurality of electrically resistive heating elements disposed within the airway;
        the substance disposed on at least one of the heating elements; and
        an actuation mechanism configured to transfer energy from the power source to each of the plurality of heating elements; wherein an airflow from the inlet to the outlet of the airway causes the substance to vaporize and condense in the airflow to form a condensation aerosol.

9. The device of claim 8, further comprising an air bypass hole coupled to the outlet of the second housing.

10. A method of entraining a substance within an airflow comprising:
providing an airway comprising an inlet and an outlet;
providing a plurality of supports disposed within the airway, wherein the substance is disposed on at least one support of the plurality of supports;
releasing the substance from at least one the support into the airflow; and
routing an airflow within the airway to entrain the substance in the airflow when released from the support and to inhibit deposits of the substance on any other support.

11. The method of claim 10 wherein a first portion of the airflow passes through the airway from the inlet to the outlet and a second portion of the airflow passes through a plurality of holes and is directed transverse the first portion of the airflow toward the at least one support on which the substance is disposed to entrain the substance in the first portion of the airflow.

12. A method of producing a condensation aerosol in an airflow comprising:
providing an airway comprising an inlet and an outlet;
providing a plurality of supports disposed within the airway, wherein the substance is disposed on at least one support of the plurality of supports;
vaporizing the substance from the at least one support into the airflow; and
routing an airflow from the inlet to the outlet such that the substance forms a condensation aerosol when vaporized and the condensation aerosol is entrained in the airflow and deposits of the condensation aerosol on any other support is substantially prevented.

13. The device of claim 1 wherein the airflow routing means comprises a first airflow between the inlet and the outlet and a second airflow transverse the first airflow directed from the plurality of supports to separate the substance from the plurality of supports and to entrain the substance in the first airflow.

14. The device of claim 13 wherein the plurality of supports are disposed in series between the airway inlet and the airway outlet.

15. The device of claim 1 wherein the plurality of supports each comprise a resistive heating element and the mechanism configured to release the substance from each of the plurality of supports comprises an electric current through the resistive heating elements.

16. The device of claim 15 further comprising a power supply and a switch operatively disposed between the power supply and the plurality of resistive heating elements for selectively providing an electric current to a select heating element.

17. The device of claim 15 wherein each resistive heating element comprises a metal foil.

18. The device of claim 17 wherein the metal foil is arched.

19. The device of claim 18 wherein resistive heating elements are disposed in series between the airway inlet and the airway outlet.

20. The device of claim 5 wherein the metal foil is arched.

21. The device of claim 3 wherein the mechanism configured to vaporize the substance from each support comprises an electric current through the resistive heating element.

22. The device of claim 21 further comprising a power supply and a switch operatively disposed between the power supply and the plurality of resistive heating elements for selectively providing an electric current to a select heating element.

23. The device of claim 22 wherein the plurality of supports are disposed in series between the airway inlet and the airway outlet.

24. The method of claim 10 wherein the substance is disposed on more than one support of the plurality of supports and selectively releasing the substance from a select one of the more than one supports.

25. The method of claim 24 wherein each support comprises a resistive heating element and the releasing step comprises providing an electric current to the select one of the more than one supports.

26. The method of claim 25 wherein each resistive heating element comprises a metal foil.

27. The method of claim 26 wherein the metal foil is arched.

28. The method of claim 12 wherein the routing step comprises routing a first airflow portion through the airway from the inlet to the outlet and routing a second airflow portion transverse the first airflow portion directed from the plurality of supports to separate the condensation aerosol from the plurality of supports and to entrain the aerosol in the first airflow portion.

29. The method of claim 28 wherein the substance is disposed on more than one support of the plurality of supports and selectively vaporizing the substance from a select one of the more than one supports.

30. The method of claim 29 wherein each support comprises a resistive heating element and the vaporizing step comprises providing an electric current to the select one of the more than one supports.

31. The method of claim 30 wherein each resistive heating element comprises a metal foil.

32. The method of claim 31 wherein the metal foil is arched.

33. The device of claim 5, wherein the metal foil is stainless steel.

34. The device of claim 5, wherein the thickness of the metal foil is less than 0.01 inches.

35. The device of claim 5, wherein the thickness of the metal foil is less than 0.001 inches.

36. The device of claim 5, wherein the thickness of the metal foil is less than 0.0005 inches.

37. The device of claim 5, wherein the surface area of the metal foil ranges from 0.01 cm2 to 50 cm2.

38. The device of claim 5, wherein the metal foil comprises a metal layer plated on the metal foil.

39. The device of claim 38, wherein the metal layer is chosen from gold, silver, nickel, and copper.

40. The device of claim 38, wherein the metal layer is gold.

41. The device of claim 38, wherein the thickness of the metal layer ranges from 0.001 μm to 3 μm.

42. The device of claim 20, wherein the height of the arch ranges from 0.5 mm to 2 mm.

43. The device of claim 5, wherein an impedance of the heating element is closely matched to an impedance of a power source for heating the heating element.

44. The device of claim 43, wherein the difference between the impedance of the heating element and the impedance of the power source is less than 50% of the impedance of the power source.

45. The device of claim 43, wherein the difference between the impedance of the heating element and the impedance of the power source is less than 10% of the impedance of the power source.

46. The device of claim 43, wherein the difference between the impedance of the heating element and the impedance of the power source is less than 2% of the impedance of the power source.

47. The device of claim 5, wherein the ratio of the surface area of the heating element, to the thermal mass of the heating element is greater than 10 cm$^2$/J/°C.

48. The device of claim 5, wherein the ratio of the surface area of the heating element, to the thermal mass of the heating element is greater than 100 cm$^2$/J/°C.

49. The device of claim 5, wherein the ratio of the surface area of the heating element, to the thermal mass of the heating element is greater than 500 cm$^2$/J/°C.

50. The device of claim 5, wherein the heating element can reach a temperature of at least 250° C. in less than 500 msec.

51. The device of claim 5, wherein the heating element can reach a temperature of at least 250° C. in less than 250 msec.

52. The device of claim 5, wherein the heating element can reach a temperature of at least 250° C. in less than 100 msec.

53. The device of claim 5, wherein the amount of energy to vaporize one milligram of a substance disposed on the heating element is less than 250 joules.

54. The device of claim 5, wherein the amount of energy to vaporize one milligram of a substance disposed on the heating element is less than 50 joules.

55. The device of claim 5, wherein the amount of energy to vaporize one milligram of a substance disposed on the heating element is less than 10 joules.

* * * * *